(12) United States Patent
Nikiforov et al.

(10) Patent No.: US 7,105,304 B1
(45) Date of Patent: Sep. 12, 2006

(54) PRESSURE-BASED MOBILITY SHIFT ASSAYS

(75) Inventors: Theo T. Nikiforov, San Jose, CA (US); Jill M. Baker, Menlo Park, CA (US); Sansan Lin, Palo Alto, CA (US); J. Wallace Parce, Palo Alto, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 580 days.

(21) Appl. No.: 09/993,314

(22) Filed: Nov. 5, 2001

Related U.S. Application Data

(60) Provisional application No. 60/246,617, filed on Nov. 7, 2000.

(51) Int. Cl.
  *G01N 33/53* (2006.01)
  *C12M 3/00* (2006.01)

(52) U.S. Cl. ............... 435/7.1; 435/287.9; 435/7.8; 435/7.92

(58) Field of Classification Search ............ 435/4, 435/7.1, 7.2, 7.21, 7.4, 7.8, 7.9, 7.91, 7.92, 435/7.93, 7.95; 436/514, 518, 523, 524, 436/527, 531, 532, 533, 536, 538, 540, 541; 422/50, 56, 59; 530/416
See application file for complete search history.

(56) References Cited

U.S. PATENT DOCUMENTS

| | | | | |
|---|---|---|---|---|
| 3,591,010 A * | 7/1971 | Pall et al. ............... | 210/493.1 |
| 4,053,512 A * | 10/1977 | Panzer et al. ............. | 525/353 |
| 4,448,493 A * | 5/1984 | Matsudaira et al. ........ | 359/268 |
| 5,114,855 A * | 5/1992 | Hu et al. ................ | 435/403 |
| 5,203,976 A * | 4/1993 | Parsi et al. .............. | 204/632 |
| 5,508,273 A * | 4/1996 | Beers et al. .............. | 514/141 |
| 5,942,443 A | 8/1999 | Parce et al. | |
| 6,235,471 B1 | 5/2001 | Knapp et al. | |
| 6,274,337 B1 | 8/2001 | Parce et al. | |
| 6,287,520 B1 | 9/2001 | Parce et al. | |
| 6,287,774 B1 | 9/2001 | Nikiforov | |
| 6,306,590 B1 | 10/2001 | Mehta et al. | |
| 6,329,357 B1 * | 12/2001 | Norman et al. ............. | 514/167 |
| 6,440,645 B1 * | 8/2002 | Yon-Hin et al. ............ | 430/322 |
| 6,440,725 B1 * | 8/2002 | Pourahmadi et al. ...... | 435/288.5 |
| 6,499,499 B1 * | 12/2002 | Dantsker et al. ............ | 137/1 |

FOREIGN PATENT DOCUMENTS

| | | | |
|---|---|---|---|
| JP | 50000093 | * | 1/1975 |
| WO | WO 98/45481 | * | 10/1998 |
| WO | WO 98/45481 A1 | | 10/1998 |
| WO | WO 98/56956 A1 | | 12/1998 |
| WO | WO 0050172 A1 | | 8/2000 |

OTHER PUBLICATIONS

Grate et al. (1999) "Sequential Injection Separation and Sensing." *Chemical Microsencors and Applications !!* 3857:70-73.

(Continued)

*Primary Examiner*—Long V. Le
*Assistant Examiner*—Ann Y Lam
(74) *Attorney, Agent, or Firm*—Donald R. McKenna; Ann C. Petersen

(57) ABSTRACT

Methods for chromatographically separating materials, including the separation of materials in kinase or phosphatase assays, in microfluidic devices under positive or negative fluid pressure. Devices and integrated systems for performing chromatographic separations are also provided.

31 Claims, 7 Drawing Sheets

OTHER PUBLICATIONS

Weiss (1995) *Ion Chromatography* VCH Publications, Chapter 3, pp. 25-208.

Zhang and Wang (1998) *J. Chromatogr* 712:73.

Lane et al. (1994) *J. Cell Biol.* 125:929-943.

Jeno et al. (1993) *Anal. Biochem* 215:292-298.

Berna et al. (1997) "Polyol Promoted Adsorption of Serum Proteins to Amphiphilic Agarose Based Adsorbents." *J. Chromatogr.* 764:193-200.

Berna et al. (1996) "Cosolvent-Induced Adsorption and Desorption of Serum Proteins on an Amphipholic Mecaptomethylene Pyridine-Derivatized Agarose Gel." *Arch. Biochem. And Biophys.* 330:188-192.

Goheen and Gibbins (2000) "Protein losses in ion-exchange and hydrophobic interaction high-performance liquid chromatography." *J. Chromatogr.* 890(1):73-80.

Teal et al. (2000) Native purification of biomolecules with temperature-mediated hydrophobic modulation liquid chromatography. *Anal Biochem.* 283(2):159-65.

Toshima et al. (2000) "A New Model of Cerebral Microthromobsis in Rats and the Neuroprotective Effect of a Rho-Kimase Inhibitor." *Stroke* 31(9):2245-2250.

Murata et al. (2000) "Vascular endothelial growth factor (VEGF) enhances the expression of receptors and activates mitogen-activated protein (MAP) kinase of dog retinal capillary endothelial cells." *J. Ocul. Pharmacol. Ther.* 16(4):383-391.

Vermes et al. (2000) "Particulate wear debris activates protein tyrosine kinases and nucleas factor kappaB, which down-regulates type I collagen synthesis in human osteoblasts." *J. Bone Miner Res.* 15(9):1756-1765.

Martelli et al. (2000) "Phosphatidylinositol 3-kinase translocates to the nucleus of osteoblast-like MC3T3-E1 cells in response to insulin-like growth factor I and platelet-derived growth factor but not to the proapoptotic cytokikn tumor necrosis factor alpha." *J. Bone Miner Res.* 15(9):1716-1730.

Caverzasio et al. "Evidence for the involvement of two pathways in activation of extracellular signal-regulated kinase )Erk) and cell proliferation bu Gi and Gq protein-coupled receptors in osteoblast-like cells." *J. Bone Miner Res.* 15(9):1697-1706.

Slevin et al. (2000) "Activation of MAP kinase (ERK-1/Erk-2), tyrosine kinase and VEGF in the human brain following acute ischaemic stroke." *Neuroreport* 11(12):2759-2764.

Munoz et al. (2000) "Increase in the expression of the neuronal cyclin-dependent protein kinase cdk-5 during differentiation of N2A neuroblastoma cells." *Neuroreport* 11(12)"2733-2738.

Rochette-Egly et al. (2000) "The AF-1 and AF-2 activating domains of retinoic acid receptor-alpha (RARalpha) and their phosphorylation are differently involved in parietal endodermal differentiation of F9 cells and retinoid-induced expression of target genes." *Mol. Endocrinol* 14(9):1398-410.

Begum et al. (2000) "Regulation of Myosin-Bound Protein Phosphatase by Insulin in Vascular Smooth Muscle Cells: evaluation of the role of Rho kinase and phosphatidylinositol-3-kinase-dependent signaling pathways." *Mol. Endocrinol* 14(9):1365-1376.

Stofega et al. (2000) "Mutation of the SHP-2 binding site in growth hormone (GH) receptor prolongs GH-promoted tyrosyl phosphorylation of GH receptor, JAK2, and STAT5B." *Mol Endocrinol* 14(9):1338-50.

Wang et al. (2000) "Thyrotropin-releasing hormone stimulates phosphorylztion of the epidermal growth factor receptor in GH3 pituitary cells." *Mol. Endocrinol* 14(9):1328-1337.

Wilmanns et al. (2000) "Activation of calcium/calmodulin regulates kinases." *Cell Mol Biol* 46(5):883-894.

Genet et al. (2000) "Effect of free radicals on cytosolic creatine kinase activities and protein by antioxidant enzymes and sulfhydryl compounds." *Mol Cell Biochem* 210(1-2):23-28.

Kaytor et al. (2000) "An indirect role for upstream stimulatory factor in glucose-mediated induction of pyruvate kinase and S14 gene expression." *Mol. Cell Biochem* 210(1-2):13-21.

Middleton (1990) "Hexokinases and glucokinases." *Biochem. Soc. Trans.* 18:180-183.

Lindberg et al. (1992) "Dual-specificity protein kinases: will any kydroxyl do?" *Trends Biochem. Sci* 17:114-119.

Knighton et al. (1991) "Crystal structure of the catalytic subunit of cAMP-dependent protein kinase." *Science* 253-407-414.

Featherstone and Russel (1991) "Fission yeast p107$^{wee1}$ mitotic inhibitor os a tyrosine/serine kinase." *Nature* 349:808-811.

Kemp and Pearson (1990) "Protein kinase recognition sequence motifs." *Trends Biochem. Sci.* 15:342-346.

Pagani et al.(2001) "'%'-Nucloeotidase in the detection of increased activity of the liver form of alkaline phosphatase in serum." *Clin. Chem.* 47(11):2046-2048.

Abe et al. (2001) "Extracellular matrix regulates induction of alkaline phosphatase expression by ascorbic acid in human fibroblasts." *Cell Physiol* 189(2):144-151.

Dirnbach et al. (2001) "Mg2+binding to alkaline phosphatase correlates with slow changes in protein lability." *BiochemistryBiochemistry* 40(37):11219-11226.

Tiedtke et al. (1983) "Acid phosphatase associated with dischaging secretory vesicles (mucocysts) of *Tetrahymena thermophila.*" *Eur. J. Cell Biol* 30(2):254-257.

Luchter-Wasylewska (2001) "Cooperative kenetics of human prostatic acid phosphatase." *Biochim. Biophys. Acta* 15489 (2):257-264.

Pierrugues et al. (2001) "Lipid phosphate phosphatase in *Araabidopsis*. Regulation of the AtLPP1 gene is response to stress." *J. Bio. Chem* 276(23):20308.

Wang et al. (2001) "Protein phosphatase 1alpha-mediated stimulation of apoptosis is associated with dephosphorylation of the reinodlastoma protein." *Oncogene* 20(43):6111-6122.

Tan et al. (2001) "Phosphorylation of a novel myosin binding subunit of protein phosphatase 1 reveals a conserved mechanism in the regulaion of actin cytosytoskleton." *J. Biol. Chem* 276(24):21209-21216.

Moore et al. (1985) "The involvement of glucose-6-phosphatase in mucilage secretion by root cap cells of *Zea mays.*" *Ann. Bot. (Lond)* 56:139-142.

Ichai et al. (2001) "Glucose 6-phosphate hydrolysis is activated by glucagon in a low tempature-sensitive mannor." *J. Biol. Chem* 276(30)28126-28133.

Ye et al. (1996) "Inducer expulsion and the occurrence of an HPr(Ser-P)-activated sugar-phosphate phosphatase in *Enterococcus faecalis* and *Streptococcus pyogenes.*" *Microbiology* 142(Pt. 3):585-592.

* cited by examiner

PRESSURE-BASED MOBILITY SHIFT ASSAYS

CROSS-REFERENCES TO RELATED APPLICATIONS

Pursuant to 35 U.S.C. §§ 119 and/or 120, and any other applicable statute or rule, this application claims the benefit of and priority to U.S. Ser. No. 60/246,617, filed on Nov. 7, 2000, the disclosure of which is incorporated by reference.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Chromatography is a powerful separation technique widely used in various scientific disciplines, including many pharmaceutical, chemical, and biotechnological analyses and preparative processes. In general, chromatography embraces a diverse collection of techniques for separating closely related components of complex mixtures by passing a mobile phase, which contains the sample to be separated, through an immiscible stationary phase. Mobile and stationary phases are selected such that sample constituents distribute themselves between the two phases to varying degrees. Each individual substance moves as a zone progressing at a fraction of the mobile phase rate. One constituent separates from others because this fraction varies according to the particular substance, depending on their partition coefficients between the two phases. Those constituents that strongly interact with, or adsorb on, the stationary phase advance at slower rates, if at all, than those with weaker molecular interactions do, thus effecting separation. The separated constituents are then accessible for subsequent downstream analysis.

Various characteristics provide a basis for separating materials. For example, ion chromatography generally involves the separation of sample constituents based upon their net charge. This sensitive technique is frequently used to separate organic or inorganic ions and even nonionic substances. It typically entails flowing the mobile phase through an ion exchanger having a net charge opposite from components to be separated from a sample mixture whether it is the material of interest or impurities and subsequently eluting the components from the exchanger. Other chromatographic techniques exploit differences, other than net charge or polarity, among sample components, such as distinguishing binding affinities for a selected stationary phase, and hydrophilic or hydrophobic characteristic variations, among other properties.

Many different chromatographic techniques are generally known and described in the literature, including, e.g., Matejtschuk (Ed.), *Affinity Separations: A Practical Approach* (1997) IRL Press, Oxford; Scouten, *Affinity Chromatography: Bioselective Adsorption on Inert Matrices* (1981) John Wiley & Sons, New York; Bickerstaff (Ed.) *Immobilization of Enzymes and Cells: Methods in Biotechnology* 1 (1997) Humana Press, Towana, N.J.; Hermanson et al., *Immobilized Affinity Ligand Techniques* (1992) Academic Press, San Diego; *Hydrophobic Interaction Chromatography: Principles and Methods* (1993) Pharmacia; Brown, *Advances in Chromatography* (1998) Marcel Dekker, Inc., New York; Fallon, Booth, and Bell (Eds.), *Applications of HPLC in Biochemistry: Laboratory Techniques in Biochemistry and Molecular Biology* (1987) Elsevier Science Publishers, Amsterdam; Lough and Wainer (Eds.), *High Performance Liquid Chromatography: Fundamental Principles and Practice* (1996) Blackie Academic and Professional, London; Mant and Hodges (Eds.), *High Performance Liquid Chromatography of Peptides and Proteins: Separation, Analysis and Conformation* (1991) CRC Press, Boca Raton; Katz (Ed.), *High Performance Liquid Chromatography: Principles and Methods in Biotechnology* (1996) John Wiley & Sons, Inc., Chichester, England; Weiss, *Ion Chromatography*, $2^{nd}$ ed. (1995) VCH, New York; *Ion-Exchange Chromatography: Principles and Methods* (1991) Pharmacia; Smith, *The Practice of Ion Chromatography* (1990) Krieger Publishing Company, Melbourne, Fla.; and Bidlingmeyer, *Practical HPLC Methodology and Applications* (1992) John Wiley & Sons, Inc., New York.

In general, additional chromatographic techniques would be desirable. The present invention provides new methods and devices for performing chromatographic separations that have many significant advantages over current separation approaches. These and a variety of additional features will become apparent upon complete review of the following description.

SUMMARY OF THE INVENTION

The present invention generally relates to the separation of materials, such as the separation of products from substrates or reactants. In particular, the invention provides methods and integrated systems for separating selected materials from one another in microfluidic devices using chromatographic separation methods. For example, certain specific analytical methods of the invention relate to the separation of reactants, enzymes, and products in kinase or phosphatase assays. As discussed herein, the invention includes many advantages relative to other separation techniques, such as those based on electrophoretic mobility.

In one aspect, the invention relates to a method of performing a mobility shift assay in a microfluidic device. The method includes flowing a reaction mixture that includes an enzyme, an enzyme substrate, and a product through a separation region of the microfluidic device under an applied pressure to separate the product from at least one other material (e.g., the enzyme and/or unreacted enzyme substrate) based upon a net charge difference between the product and the at least one other material to produce separated materials. The separation region, which is typically disposed in a microchannel, includes an ion-exchange material. The method also includes detecting at least one of the separated materials. In some embodiments, the enzyme includes a kinase, the enzyme substrate includes a kinase substrate, and the product includes a phosphorylated product. In other embodiments, the enzyme includes a phosphatase, the enzyme substrate includes a phosphatase substrate, and the product includes a dephosphorylated product. Optionally, prior to the flowing step, the method includes flowing at least the enzyme through a first channel in fluid communication with an enzyme source into a mixing region (e.g., in a microchannel, etc.) of the microfluidic device, and flowing at least the enzyme substrate through a second channel in fluid communication with an enzyme substrate source into the mixing region in which the enzyme converts at least some of the enzyme substrate to the product to produce the reaction mixture. Other options include sampling the reaction mixture from a source external to the microfluidic device, or sampling the enzyme, the enzyme substrate, and/or an additional material from one or more sources external to the microfluidic device.

In another aspect, the invention relates to a method of performing a mobility shift assay in a microfluidic device that includes flowing a mixture including at least first and second materials through a separation region of the microfluidic device that includes an amphiphilic material under an applied pressure in which the first and second materials separate from one another in the separation region to produce separated first and second materials. Typically, the first and second materials include different net charges in solution. The method further includes detecting at least one of the separated first and second materials. In certain embodiments, the mixture includes at least a third material, which third material separates from the first and second materials in the separation region. Optionally, the first and second materials are mixed in a mixing region of the microfluidic device to produce the mixture prior to flowing through the separation region. One additional option includes sampling the first material, the second material, and/or an additional material from one or more sources external to the microfluidic device.

In one embodiment, the invention provides methods of separating materials in a microfluidic device. The methods generally include flowing first and second materials into contact in a mixing region (e.g., a microchannel or other cavity) of the microfluidic device under positive or negative fluid pressure. Thereafter, the first or second material or a third material produced by contacting the first and second material is flowed, under positive or negative fluid pressure, into a microchannel that includes a separation region having a chromatographic material. At least one of the first, second, or third material is separated from other material in the separation region, and the separated material is detected. The methods optionally include flowing materials in the microfluidic device in the absence of an applied electric field, or flowing materials in the microfluidic device under a simultaneously applied electric field. The positive or negative pressure is typically produced by a vacuum pump operably coupled to the microfluidic device through a port that fluidly communicates with the mixing or separation region, though other embodiments, such as micropump arrangements are also optionally used. Additionally, the second flowing step also typically includes flowing eluents or separation buffers into the separation region from microchannels in fluid communication with the separation region. For example, a concentration of the eluents or separation buffers flowed into the separation region is optionally varied, e.g., to control separation of materials within the separation region. The detecting step generally includes, e.g., optical, spectroscopic, fluorescent, mass, luminescent, or other detection approaches. Optionally, the first, second, or third materials include a label, e.g., to assist in detection. One or several different material(s) is/are optionally separated according to these methods.

In certain embodiments, the first, second, or an additional material (e.g., a modulator, an inhibitor, an antagonist, an agonist, an eluent, a separation buffer, or the like) is sampled from sources external to the microfluidic device. For example, the sources are optionally present in a microtiter dish and the microfluidic device further includes external capillary elements in fluid communication with the mixing or separation region. This method of sampling the materials includes, e.g., contacting the external capillary elements to the sources and drawing fluid out of the sources, into the external capillary elements, and into the mixing or separation region.

The methods of the present invention include assorted approaches for separating materials in microfluidic devices. For example, the first, second, or third material is optionally separated from the other material based upon distinguishing properties of the first, second, third, or additional materials. Example distinguishing properties include, e.g., net charge, polarity, polarizability, binding affinity, hydrophobic properties, hydrophilic properties, amphiphilic properties, electrostatic properties, or the like. In several embodiments, separation is based upon net charge differences in which, e.g., the third material (e.g., a product) has a different charge in solution than the first or second materials (e.g., reactants, enzymes, etc.).

The chromatographic materials used in the invention are disposed within the separation region using alternative techniques. For example, an inner surface of the separation region optionally includes the chromatographic material, or the chromatographic material is optionally coated on the inner surface of the separation region. In other embodiments, the methods include, e.g., flowing the chromatographic material into the separation region, flowing a second chromatographic material into the separation region, or flowing, e.g., three or more chromatographic materials or surface coatings into the separation region. For example, each chromatographic material or surface coating is optionally sequentially flowed into the separation region, e.g., in which each sequentially flowed chromatographic material or surface coating coats or modifies an inner surface of the separation region or a previously flowed material which coats the inner surface of the separation region. The chromatographic material is alternatively continuously flowed into the separation region for a selected period of time, or multiple aliquots of the chromatographic material are flowed into the separation region. The chromatographic material is optionally stored in a reservoir that is fluidly coupled to the separation region. Appropriate chromatographic materials are typically selected according to the distinguishing features for the materials to be separated. Optionally, a plurality of microbeads or a gel includes the chromatographic material (e.g., covalently or otherwise attached thereto).

The present invention also relates to a device or integrated system. The system includes a body structure that has at least two intersecting microchannels fabricated therein and a source of a first chromatographic material coupled to at least one of the at least two channels. The system also includes a pressure source for applying positive or negative pressure to at least one of the two intersecting channels and a controller. The controller optionally dispenses a first aliquot of the first chromatographic material into at least a first of the at least two intersecting channels. The device or system alternatively includes flowing materials in the microfluidic device in the absence of an applied electric field, or flowing materials in the microfluidic device under a simultaneously applied electric field.

In certain embodiments, the system includes a first source of a first material and a second source of a second material, in which, during operation of the device, the first and second materials are flowed into a mixing region in at least one of the at least two intersecting channels. For example, the first or second source can be present in a microtiter dish. In this embodiment, the microfluidic device also typically includes an external capillary element that samples the first or second material from the microtiter dish. For example, during operation of the device, the external capillary element optionally draws fluid into the microfluidic device by applying negative pressure at the source of the first or second material. In an alternative embodiment, materials are stored dried on any of a variety of substrates (e.g., membranes, slides, plates, etc.). The materials are optionally accessed, e.g., using a re-solubilization pipettor fluidly coupled to, or integrated into, the microfluidic device. The device also optionally includes a reservoir on an upper surface of the device that includes a source of the first or second material (or of additional materials).

The intersecting channels of the device or integrated system of the invention typically include a mixing region and a separation region. The source of the first chromatographic material is optionally fluidly coupled to the separation region, and the controller, during operation of the device, typically flows aliquots of the first chromatographic material into the separation region. The controller also optionally directs flow of first and second materials from sources of the first and the second materials into the mixing region in which the first and second materials are mixed. Additionally, the first or second materials, or a third material produced by contacting the first and second materials are flowed into the separation region in which at least one of the first, second, or third materials are separated from at least one other material based upon distinguishing properties of the first, second, third, or an additional material. The distinguishing properties include, e.g., a net charge, a polarity, a polarizability, a binding affinity, a hydrophobic property, a hydrophilic property, an amphiphilic property, an electrostatic property, or the like.

Many different materials are optionally separated using the devices and integrated systems of the present invention. For example, the first, second, or a third material produced by contacting the first and second materials, optionally includes, e.g., a biological molecule, an artificial molecule, an ion, a polar molecule, an apolar molecule, an antibody, an antigen, an inorganic molecule, an organic molecule, a drug, a receptor, a ligand, a neurotransmitter, a cytokine, a chemokine, a hormone, a particle, a bead, a functionalized bead, a liposome, a cell, a nucleic acid, DNA, RNA, an oligonucleotide, a ribozyme, a protein, a phosphoprotein, a glycoprotein, a lipoprotein, a peptide, a phosphopeptide, a glycopeptide, a lipopeptide, an enzyme, an enzyme substrate, a product, a carbohydrate, a lipid, a label, a dye, a fluorophore, or the like.

The chromatographic material of the device or integrated system typically includes an ion exchange material, a hydrophobic adsorbent material, a hydrophilic adsorbent material, an affinity adsorbent material, a metal chelating adsorbent material, an amphiphilic adsorbent material, an electrostatic adsorbent material, a chemisorbent, an immobilized enzyme, an immobilized receptor, an immobilized antibody, or an immobilized antigen. For example, an inner surface of at least one of the microchannels optionally includes the first chromatographic material, or the first chromatographic material is optionally coated on an inner surface of at least one of the microchannels. In certain embodiments, an appropriate chromatographic material includes, e.g., a polyarginine, a polylysine, a modified polyacrylamide, a modified dimethylacrylamide, a nonionic detergent, an ionic detergent, or the like. Additionally, a polyacrylamide or a dimethylacrylamide for use as a chromatographic material is optionally modified (e.g., via covalent attachment, via adsorption, or the like) by additives (e.g., anionic or cationic additives). Optionally, a plurality of microbeads or a gel includes the chromatographic material (e.g., covalently or otherwise attached thereto).

In certain embodiments, the device or integrated system includes a source of at least a second chromatographic material in which the source is fluidly coupled to at least one of the at least two intersecting microchannels. Alternatively, the first chromatographic material is stored in a reservoir, which reservoir is fluidly coupled to a separation region located in at least one of the at least two intersecting microchannels. In addition, the system typically includes a source of an eluent or separation buffer, which source is fluidly coupled to at least one of the at least two intersecting microchannels. For example, during operation of the device, the controller generally varies a concentration of the eluent or separation buffer which the controller flows into a separation region to control separation of materials within the separation region. The device or integrated system of the present invention also typically includes a detector mounted proximal to a detection region of the microfluidic device in which the detection region is within or fluidly coupled to at least one of the at least two intersecting microchannels.

The present invention also provides methods of performing a kinase assay in a microfluidic device. The methods include flowing a kinase (e.g., a protein kinase, a protein kinase A, a nucleic acid kinase, or the like) and a kinase substrate into contact to produce a phosphorylated product, and flowing at least the phosphorylated product through a separation region of a microchannel in the microfluidic device under pressure. Essentially any kinase is suitable for use in the assays of the present invention including those comprising enzyme classification (EC) numbers, such as 2.1, 2.7, 2.8, 3.1, 3.4, 4.1, 6.2, or the like. The separation region includes an ion-exchange material (e.g., a polyarginine, a polylysine, a modified polyacrylamide, a modified dimethylacrylamide, or the like), which effects separation of the phosphorylated product from at least one other material based upon a difference in net charge of the phosphorylated product and the at least one other material. Optionally, the ion-exchange material includes a polyacrylamide or a dimethylacrylamide modified (e.g., via covalent attachment, via adsorption, or the like) by one or more anionic or cationic additives. In certain embodiments, the ion-exchange material is covalently or otherwise attached to a plurality of microbeads or a gel. In addition, the methods optionally include flowing the ion-exchange material into the separation region. Furthermore, the methods also typically include detecting the resulting separated product.

In one embodiment, the methods of performing a kinase assay optionally include flowing the kinase through a first channel fluidly coupled to a first source of the kinase into a mixing region in the microfluidic device. Thereafter, the kinase substrate is typically flowed through a second channel fluidly coupled to a first source of the kinase substrate and, in turn, contacting the kinase in the mixing region and producing the phosphorylated product. The methods also typically include detecting the phosphorylated product or the kinase substrate. Similarly, the invention also provides methods of performing a phosphatase assay in a microfluidic device.

Many additional aspects of the invention will be apparent upon review, including uses of the devices and systems of the invention, methods of manufacture of the devices and systems of the invention, kits for practicing the methods of the invention and the like. For example, kits comprising any of the devices or systems set forth above, or elements thereof, in conjunction with packaging materials (e.g., containers, sealable plastic bags etc.) and instructions for using the devices, e.g., to practice the methods herein, are also contemplated.

DETAILED DISCUSSION OF THE INVENTION

Figure 1:
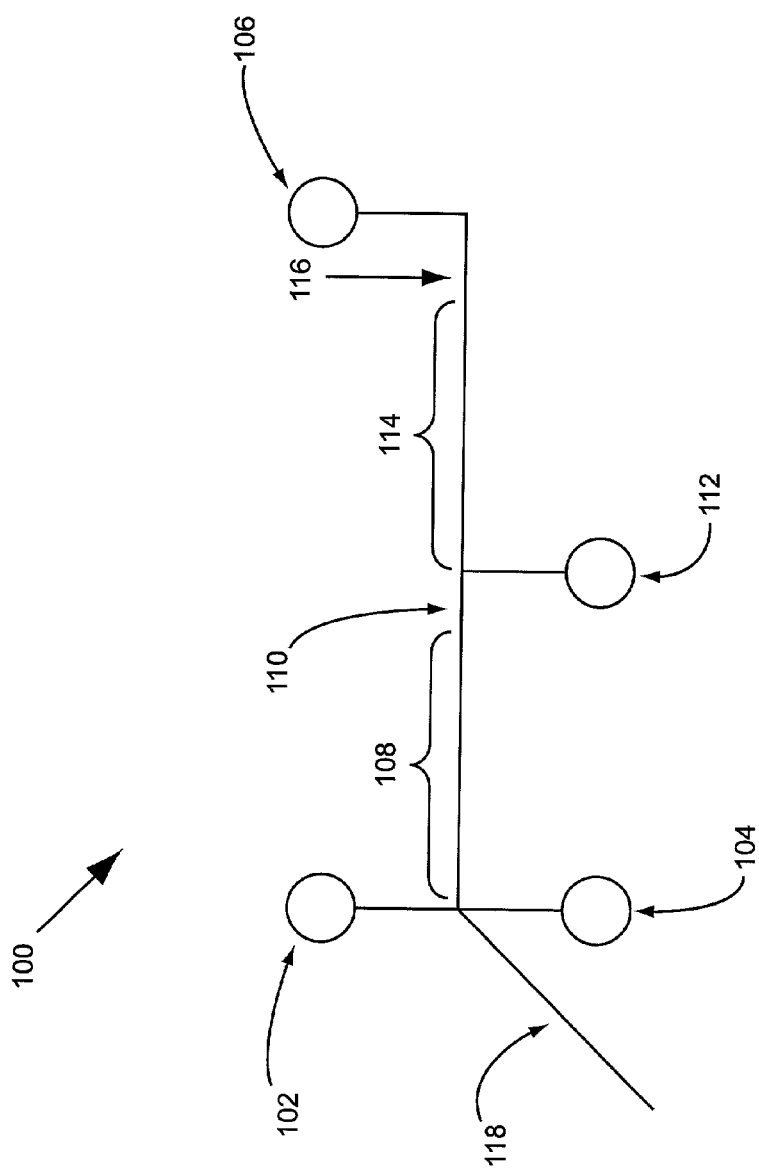
FIG. 1 schematically illustrates a device for high-throughput screening based on ion-exchange-induced mobility shifts.

Before describing the present invention in detail, it is to be understood that this invention is not limited to particular compositions, devices, or systems, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which the invention pertains. As used in this specification and the appended claims, the singular forms "a," "an," and "the" include plural referents unless the content clearly dictates otherwise. Thus, for example, reference to "an enzyme" or "an enzyme substrate" includes a combination of two or more enzymes, two or more enzyme substrates, or the like.

The present invention generally provides improved methods, and related devices, for separating materials in microfluidic devices. Materials, such as two or more sets of molecules of interest, are separated according to their net charge or other distinguishing affinities for a surface or a surface coating. In particular, constituent materials typically include different net charges or other distinguishing properties that cause certain constituents to interact to a greater extent than others with the surface or coating, which typically includes, e.g., an ion-exchange, an amphiphilic, or other chromatographic material.

In contrast to mobility shift approaches based on changes in electrophoretic mobilities, where the important parameters are the electrophoretic mobilities of, e.g., the reactants and products, and therefore their charge-to-mass ratios, in the present invention the determining factor is simply the net charge on the molecules, or another distinguishing property, such as binding affinity for a chromatographic material. This results in many advantages relative to electrophoretic techniques including simplification of overall systems, because external electric fields are not required to achieve separation. The absence of applied electric fields also eliminates problems associated with the electroosmotic properties of certain microfluidic channels. Moreover, the surface properties of the separation part of the device are controlled relatively easily by coating them with different polymers possessing, e.g., the desired ion-exchange or amphiphilic properties. In addition, separations may be further affected by controlling the ionic strength or concentration of the separation buffer, which is optionally introduced from an intersecting side channel at the beginning of the separation channel.

The following provides details regarding various aspects of the methods of separating materials, including chromatographic material selection and disposition, flowing fluidic materials under pressure in microfluidic devices, and reagent sampling. It also provides details pertaining to the methods of performing kinase or phosphatase assay separations and to high-throughput integrated systems that are optionally used to separate selected materials from one another in the microfluidic devices.

Separation Methods

The methods of the present invention relating to separating materials in a microfluidic device generally include flowing first and second materials into contact in a mixing region, such as a microchannel or other cavity, of the device. The first or second material is typically flowed into the mixing region by applying positive or negative fluid pressure to the materials. Thereafter, the first or second material (e.g., enzymes, substrates, reactants, or the like) or a third material produced by contacting the first and second materials is flowed into a microchannel that includes a separation region. In certain embodiments, more than one product is formed by contacting the first and second materials. These are also optionally separated according to the methods described herein. The separation region of the microchannel includes a chromatographic material, that is either integral with, or coats, a surface within the channel. At least one of the first, second, or third material is separated from other material (e.g., the first material, the second material, the third material, or another material) in the separation region, and a resulting separated product is detected (e.g., by optical, spectroscopic, fluorescent, mass, luminescent, or another form of detection). In many embodiments, at least one of the first, second, or third materials optionally includes a label. The methods optionally include flowing materials in the microfluidic device in the absence of an applied electric field, or flowing materials in the microfluidic device under a simultaneously applied electric field. Other methods, such as sequential injection separations and renewable column separation, are also practiced according to the methods of the invention and are described further in, e.g., Grate et al., (1999) "Sequential Injection Separation and Sensing," in *Chemical Microsensors and Applications II* (from the proceedings of SPIE) 3857:70–73.

Aside from isocratic elutions in which the constituent materials to be separated have constant partition coefficients throughout the separation, the application of eluent gradients (e.g., continuous, stepped, or the like) are often appropriate. A gradient in eluent composition is typically used which becomes progressively more strongly eluting as the separation proceeds. To illustrate, in the case of many proteins there may be no conditions available in which a finite partition coefficient is observed between the mobile and stationary phases. For example, with ion exchangers, although the partition coefficient of, e.g., a monoanionic material typically varies linearly with the concentration of a competing monoanion in the eluent, that of a material that exchanges with x univalent anions may vary with the xth power of the concentration of competing monoanion. For proteins, there is generally no simple relation to net charge, but many singly charged eluent ions may exchange for one protein molecule. Thus, the partition coefficient changes sharply with concentration of the competing ion. A small change in this concentration effectively changes the protein from being completely adsorbed onto the chromatographic material in the separation region to being negligibly adsorbed. Nonetheless, protein separations are feasible, because desorption typically occurs for different proteins at different points in the gradient. As a result, the methods of the present invention generally include controlling the separation of materials and/or the elution of adsorbed materials from chromatographic materials in the separation region by varying the concentration of eluent (e.g., applying an ascending or a descending eluent gradient) flowed into the separation region from microchannels in fluid communication with the separation region. Specifically, separations are typically controlled and/or effected by, e.g., varying separation buffer or eluent pH, ionic strength, or the like. Appropriate eluents and separation buffers are well-known in the art.

The basis for separating materials according to the invention includes various distinguishing properties, such as net charge, polarity, polarizability, binding affinities, hydrophobic properties, hydrophilic properties, amphiphilic properties, electrostatic properties, or the like. These properties create distinguishing affinities of sample components for a given chromatographic material (i.e., an ion exchange material, a hydrophobic adsorbent material, a hydrophilic adsorbent material, an affinity adsorbent material, a metal chelating adsorbent material, an amphiphilic adsorbent material, an electrostatic adsorbent material, a chemisorbent, an immobilized enzyme, an immobilized receptor, an immobilized antibody, an immobilized antigen, or the like). As a result, the methods generally include contacting the first and second materials to produce at least a third material (e.g., a reaction product) that has a net charge in solution, or another distinguishing property, that is different from a net charge in solution of the first or second material (or an additional product or other material).

Materials, such as proteins, are optionally separated according to the methods of the present invention on the basis of net charge differences by ion chromatography. For example, if a protein has a net positive charge at pH 7, it will usually bind to a chromatographic material (e.g., one having negatively charged functional groups, such as carboxylate groups or the like) in the separation region, whereas a negatively charged protein in the a separation region will not adsorb on the chromatographic material. A positively charged protein bound to such a chromatographic material is then optionally eluted by increasing the concentration of, e.g., NaCl or another salt in the eluting buffer. $Na^+$ ions compete with positively charged groups on the protein for binding to the chromatographic material in the separation region. Proteins that have relatively low net positive charge densities will elute first, followed by those having relatively high charge densities. Anionic materials are optionally separated according to the methods of the invention by using chromatographic materials having, e.g., positively charged diethyl-aminoethyl functional groups or the like. Cationic materials are optionally separated on chromatographic materials having, e.g., negatively charged carboxymethyl functional groups or the like. Other exemplary ionic exchange chromatographic materials are described further below. Many of these and others appropriate to the invention are known to those of skill. Additional details pertaining to ion chromatography are described in, e.g., Jandik and Cassidy, *Advances in Ion Chromatograhy* (1989) Waters Corporation, Weiss, *Ion Chromatography* (1995) VCH Publications, Fritx and Gjerde, *Ion Chromatograhy*, $3^{rd}$ Ed. (2000) John Wiley & Sons, and Tarter, *Ion Chromatography* (1987) Marcel Dekker.

Affinity chromatography is another powerful separation technique that is optionally used to separate many different types of materials, including proteins. This separation method takes advantage of the high affinity of, e.g., many proteins for specific functional groups, such as receptors for their agonists, antibodies for their cognate antigens, proteins with metal binding sites for their metal ions (e.g., a chelating adsorbent material), and enzymes for their substrates, cofactors, effectors, inhibitors, or the like (e.g., a specific protease for a protease inhibitor, or the like). Note, that either the protein or its particular ligand is optionally incorporated as the functional unit of the chromatographic material. Adsorbents are also optionally constructed to include a group that is close enough to the natural ligand of the protein such that the adsorbent binds the protein specifically. Additionally, a spacer arm is optionally attached so that the site on the protein can be reached, e.g., even if the binding site is in a cavity in the protein. Adsorbed proteins are optionally desorbed by, e.g., an increase of ionic strength or by competition for the site on the protein with a soluble ligand. Other details regarding affinity-based separations is described in, e.g., Bailon et al. (Edt), *Affinity Chromatography: Methods and Protocols* (*Methods in Molecular Biology*), (2000) Humana Press, Kline, *Handbook of Affinity Chromatography* (1993) Marcel Dekker, Inc., and Chaiken (Edt), *Analytical Affinity Chromatography* (1987) CRC Press.

Other separation techniques optionally used to practice the methods of the present invention include, e.g., hydrophilic, amphiphilic, hydrophobic interaction chromatography, or the like. Hydrophilic interaction chromatography is a variant of normal-phase chromatography. Elution occurs roughly in the opposite order of reverse phase chromatography, that is, the least polar compounds tend to elute first, the most polar last (i.e., elution is in the order of increasing polarity). Hydrophilic interaction chromatography generally involves chromatographic materials (i.e., stationary phases) that are highly polar (e.g., polyhydroxyethyl groups, or the like). The technique typically works well, e.g., for lipopeptides, amyloid peptides, histones, membrane proteins, oligonucleotides or analogs thereof, complex carbohydrates, phospholipids, glycopeptides, phosphopeptides, synthetic peptides, natural peptides, or the like. Hydrophilic-based separation techniques generally elute with decreasing gradients of, e.g., acetonitrile, propanol, or the like in aqueous buffers. Additional details regarding these techniques are provided in, e.g., Zhang and Wang, (1998) *J. Chromatogr.* 712:73, Lane et al., (1994) *J. Cell Biol.* 125:929, Jeno et al., (1993) *Anal. Biochem.* 215:292; Alpert (1990) *J. Chromatogr.* 499:177–196; Jenoe et al., (1993) *Anal. Biochem.* 215:292–298; Berna et al., (1997) "Polyol Promoted Adsorption of Serum Proteins to Amphiphilic Agarose Based Adsorbents" *J. Chromatogr.* 764:193–200 and Berna et al., (1996) "Cosolvent-Induced Adsorption and Desorption of Serum Proteins on an Amphiphilic Mercaptomethylene Pyridine-Derivatized Agarose Gel. " *Arch. Biochem. And Biophys.* 330:188–192.

Hydrophobic interaction chromatography typically involves the use of chromatographic materials that have non-polar alkane or aromatic functional groups, such as phenyl, n-octyl, n-butyl, or the like. In general, the longer the alkane, or the larger the aromatic group, the stronger the binding interaction will be. Many proteins are able to sequester these functional groups on their surfaces and this exclusion from the solvent provides the basis of the binding energy. This interaction is typically enhanced by increasing ionic strength such that proteins are generally bound under high salt concentrations and eluted under low salt conditions. As a result, this techniques is typically used not only to purify a protein sample, but also to desalt the sample. Due to the nature of hydrophobic interactions and ionic strength, hydrophobic interaction chromatography and ion chromatography are optionally used sequentially. To illustrate, after a hydrophobic separation region is eluted in low salt, the collected sample is optionally run through a separation region that includes a chromatographic material with ion exchange properties, since low salt conditions are typically used to bind materials to ion exchange chromatographic materials. Conversely, following an ion exchange separation a protein sample is typically in high salt conditions which are usually favorable for binding to a hydrophobic chromatographic material. Other details pertaining to hydrophobic interaction chromatography are included in, e.g., Goheen and Gibbins (2000) "Protein losses in ion-exchange and hydrophobic interaction high-performance liquid chromatography," *J. Chromatogr.* 890(1):73–80 and Teal et al., (2000) "Native purification of biomolecules with temperature-mediated hydrophobic modulation liquid chromatography," *Anal. Biochem.* 283(2):159–65.

FIG. 1 schematically illustrates one embodiment of, e.g., the ion-exchange-induced mobility shift-based separation methods, described above, that are optionally used, e.g., for high-throughput screening. As described herein, many other distinguishing properties also optionally serve as the basis for separation. As shown, microchannel configuration 100 includes enzyme well 102 and substrate well 104 into which enzyme and substrate solutions are respectively placed. Under negative pressure applied by a vacuum at vacuum port 106, the enzyme and substrate solutions are continuously flowed from enzyme well 102 and substrate well 104, respectively, and mixed in mixing/reaction region 108 of main microchannel 110 to produce at least one reaction product.

A solution of a suitable ion-exchanger or other chromatographic material, as appropriate, is optionally placed into chromatographic material well 112 and flowed continuously into separation region 114 of main microchannel 110, during the course of the assay to effect separation of at least one of the enzyme, substrate, or reaction product from the others based upon their, e.g., respective net charges or other distinguishing properties. (FIG. 1). Alternatively, separation region 114 of main microchannel 110 is selectively modified by, e.g., coating it with, e.g., the ion-exchanger prior to commencing the assay. An additional option includes manufacturing at least separation region 114 of main microchannel 110 to, e.g., possess the desired ion-exchange characteristics (e.g., by selecting appropriate microfluidic device substrate materials). Alternative materials that are optionally used in the manufacture of microfluidic devices are described further, below.

In any event, one or more of the separated materials are detected by detector 116 disposed downstream from separation region 114 and proximal to main microchannel 110. (FIG. 1). Optionally, a modulator, an inhibitor, an antagonist, an agonist, or other material is flowed from a well on a microwell plate or another external source through capillary element 118 into mixing/reaction region 108 of main microchannel 110, e.g., to assess its impact on the assay. As used herein, a "capillary element" includes an elongated body structure having a channel (e.g., a microchannel) disposed therethrough. A capillary element is alternatively a separate component that is temporarily coupled to multiple microfluidic device body structures or an integral extension of the body structure of a single microfluidic device.

Many different materials are optionally separated according to these methods. For example, the first, second, or third material optionally includes a biological molecule, an artificial molecule, an ion, a polar molecule, an apolar molecule, an antibody, an antigen, an inorganic molecule, an organic molecule, a drug, a receptor, a ligand, a neurotransmitter, a cytokine, a chemokine, a hormone, a particle, a bead, a functionalized bead, a liposome, a cell, a nucleic acid, DNA, RNA, an oligonucleotide, a ribozyme, a protein, a phosphoprotein, a glycoprotein, a lipoprotein, a peptide, a phosphopeptide, a glycopeptide, a lipopeptide, an enzyme, an enzyme substrate, a product, a carbohydrate, a lipid, a label, a dye, a fluorophore, or the like. In one preferred embodiment, the first or second material includes, e.g., a kinase enzyme, a kinase enzyme substrate, or the like. Suitable kinase enzymes include, e.g., a protein kinase, a protein kinase A, a protein kinase B, a protein kinase C, a hexokinase, a phosphofructokinase, a phosphoglycerate kinase, a pyruvate kinase, a cyclic AMP-dependent protein kinase, a cyclic GMP-dependent protein kinase, a calmodulin-dependent protein kinase II, a casein kinase I, a casein kinase II, a glycogen synthase kinase-3, a cyclin-dependent kinase (e.g., CDK2, CDK4, CDK6, or the like), a p34/cdc2 kinase, a nucleic acid kinase, or the like. In another preferred embodiment, the materials to be separated include, e.g., a phosphatase enzyme, a phosphatase enzyme substrate, a dephosphorylated product, or the like. Essentially any phosphatase is suitable for use in the assays of the present invention, such as those comprising the EC number 3.1.3. To further illustrate, phosphatase enzymes that are optionally use in the assays described herein include, e.g., a protein phosphatase, an acid phosphatase, an alkaline phosphatase, a sugar phosphatase, a polynucleotide phosphatase, or the like.

As mentioned, in various embodiments, the first or second material is sampled from sources external to the microfluidic device. For example, the sources are optionally present in a microtiter dish and the microfluidic device further includes external capillary elements fluidly coupled to the mixing or separation region. See, FIG. 1. This method of sampling the materials includes contacting the external capillary elements to the sources and drawing fluid out of the sources under negative pressure, into the external capillary elements, and into the mixing or separating region.

Chromatographic Materials

The chromatographic materials in the present invention are optionally disposed within the separation region using various techniques. In general, chromatographic materials appropriate for the methods and devices of the present invention are known to those of skill and are readily available from many different commercial suppliers. For example, chromatographic materials are available from Sigma (St. Louis, Mo.), Suppleco (Belle Porte, Pa.), and the like. See, e.g., the 2000 Sigma Catalogue or the 1997 Suppleco Chromatography Products Catalogue). For example, an inner surface of the separation region optionally includes the chromatographic material (i.e., is integral with the surface of the microchannel at least, e.g., in the separation region). The chromatographic material is optionally applied to the microchannel surface in the separation region as a coating either before or during a particular assay. Preferred chromatographic materials suitable for use in the separations of the present invention include, e.g., polyarginine, polylysine, modified polyacrylamide, modified dimethylacrylamide, a nonionic detergent (e.g., Triton X-100™, etc.), an ionic detergent, amphiphilic materials, or the like. A polyacrylamide or a dimethylacrylamide is optionally modified (e.g., via covalent attachment, via adsorption, or the like) by anionic or cationic additives, such as those having formula (I), (II), or (III), as follows:

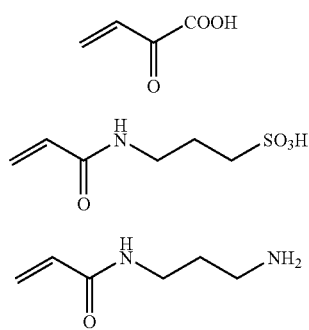

The methods of the present invention optionally include, e.g., flowing the chromatographic material into the separation region, flowing a second chromatographic material into the separation region, or flowing three or more chromatographic materials or surface coatings into the separation region to achieve, e.g., the desired ion-exchange characteristic for a particular assay, e.g., an anionic or cationic exchange surface or medium. Alternatively, the chromatographic material is continuously flowed into the separation region for a selected period of time (e.g., in which the phase that includes the material to be separated flows at a different rate than the phase that includes the continuously flowed chromatographic materials within the separation region), or multiple aliquots of the chromatographic material are flowed into the separation region. In addition, the chromatographic material is optionally stored in a reservoir that is fluidly coupled to the separation region.

In certain embodiments, the chromatographic material is covalently or otherwise attached to, e.g., a plurality of microbeads and/or a gel. In these embodiments, the functionalized microbeads or the gel is generally retained in the separation region of the device by, e.g., an modified microchannel configuration, a semi-permeable membrane, or the like. A variety of configurations for controlling particles in microfluidic systems are found in, e.g., Published PCT Application Nos. WO 00/50172 "Manipulation of Microparticles in Microfluidic Systems," by Mehta et al. and WO 00/50642 "Sequencing by Incorporation," by Parce et al. For example, a downstream end of the microchannel that includes the separation region is optionally tapered, narrowed, or otherwise altered to prevent the microbeads and/or gel from being flowed out of the region, while permitting the mobile phase to flow into and out of the separation region. Similarly, a semi-permeable membrane is optionally disposed across a downstream end of the separation region of the microchannel to retain the stationary phase.

Kinase Assays

Kinases are enzymes that catalyze the transfer of a phosphate group from ATP or other nucleoside triphosphate to a substrate. For example, hexokinase catalyzes the phosphoryl transfer from ATP to glucose to produce glucose-6-phosphate as an initial step in glycolysis. Other kinases involved in glycolysis include phosphofructokinase, phosphoglycerate kinase, and pyruvate kinase. Kinases are also involved, e.g., in protein phosphorylation by transferring the terminal phosphate from ATP to a side chain of an amino acid residue of a protein. In eukaryotic cells, protein phosphorylation serves various functions including, e.g., the phosphorylation of cell-surface receptors to produce intracellular effects, the regulation of the cell cycle, the protection of cells from toxic changes in metabolites, or the like. Many protein kinases are well-known, including, e.g., cyclic AMP-dependent protein kinases, cyclic GMP-dependent protein kinases, protein kinase C, calmodulin-dependent protein kinase II, casein kinase I, casein kinase II, glycogen synthase kinase-3, cyclin-dependent kinase, p34/cdc2 kinase, or the like.

Many kinase catalyzed reactions which are optionally modeled according to the methods of the present invention are described in, e.g., Toshima et al. (2000) "A New Model of Cerebral Microthrombosis in Rats and the Neuroprotective Effect of a Rho-Kinase Inhibitor" *Stroke* 31(9):2245–2250; Murata et al. (2000) "Vascular endothelial growth factor (VEGF) enhances the expression of receptors and activates mitogen-activated protein (MAP) kinase of dog retinal capillary endothelial cells" *J Ocul Pharmacol Ther.* 16(4):383–91, Vermes et al. (2000) "Particulate wear debris activates protein tyrosine kinases and nuclear factor kappaB, which down-regulates type I collagen synthesis in human osteoblasts" *J Bone Miner Res.* 15(9): 1756–65; Martelli et al. (2000) "Phosphatidylinositol 3-kinase translocates to the nucleus of osteoblast-like MC3T3-E1 cells in response to insulin-like growth factor I and platelet-derived growth factor but not to the proapoptotic cytokine tumor necrosis factor alpha" *J Bone Miner Res.* 15(9):1716–30, Caverzasio et al. "Evidence for the involvement of two pathways in activation of extracellular signal-regulated kinase (Erk) and cell proliferation by Gi and Gq protein-coupled receptors in osteoblast-like cells" *J Bone Miner Res.* 15(9):1697–706, Slevin et al. (2000) "Activation of MAP kinase (ERK-1/ERK-2), tyrosine kinase and VEGF in the human brain following acute ischaemic stroke" *Neuroreport* 11(12):2759–64, Munoz et al. (2000) "Increase in the expression of the neuronal cyclin-dependent protein kinase cdk-5 during differentiation of N2A neuroblastoma cells" *Neuroreport* 11(12):2733–8; Rochette-Egly et al. (2000) "The AF-1 and AF-2 activating domains of retinoic acid receptor-alpha (RARalpha) and their phosphorylation are differentially involved in parietal endodermal differentiation of F9 cells and retinoid-induced expression of target genes" *Mol Endocrinol.* 14(9):1398–410, Begum et al. (2000) "Regulation of myosin-bound protein phosphatase by insulin in vascular smooth muscle cells: evaluation of the role of Rho kinase and phosphatidylinositol-3-kinase-dependent signaling pathways" *Mol Endocrinol.* 14(9): 1365–76, Stofega et al. (2000) "Mutation of the SHP-2 binding site in growth hormone (GH) receptor prolongs GH-promoted tyrosyl phosphorylation of GH receptor, JAK2, and STAT5B" *Mol Endocrinol.* 14(9):1338–50, Wang et al. (2000) "Thyrotropin-releasing hormone stimulates phosphorylation of the epidermal growth factor receptor in GH3 pituitary cells" *Mol Endocrinol.* 14(9): 1328–37, Wilmann et al. (2000) "Activation of calcium/calmodulin regulated kinases" *Cell Mol Biol* 46(5):883–94, Genet et al. (2000) "Effects of free radicals on cytosolic creatine kinase activities and protection by antioxidant enzymes and sulfhydryl compounds" *Mol. Cell Biochem.* 210(1-2):23–8, Kaytor et al. (2000) "An indirect role for upstream stimulatory factor in glucose-mediated induction of pyruvate kinase and S14 gene expression" *Mol. Cell Biochem.* 210(1-2): 13–21, Middleton (1990) "Hexokinases and glucokinases" *Bio-* chem. Soc. Trans. 18:180–183, Lindberg et al. (1992) "Dual-specificity protein kinases: will any hydroxyl do?" *Trends Biochem. Sci.* 17:114–119, Knighton et al. (1991) "Crystal structure of the catalytic subunit of cAMP-dependent protein kinase" *Science* 253:407–414, Featherstone and Russell (1991) "Fission yeast p107$^{wee1}$ mitotic inhibitor is a tyrosine/serine kinase" *Nature* 349:808–811, and Kemp and Pearson (1990) "Protein kinase recognition sequence motifs" *Trends Biochem. Sci.* 15:342–346.

The present invention provides methods of performing kinase and other assays in microfluidic devices. The methods typically include flowing a kinase solution (e.g., a protein kinase, a protein kinase A, a nucleic acid kinase, or the like) and a kinase substrate solution into contact to produce a phosphorylated product, and flowing at least the reaction product through a separation region of a microchannel in the microfluidic device under pressure. Essentially any kinase is suitable for use in the assays of the present invention including those comprising enzyme classification (EC) numbers, such as 2.1, 2.7, 2.8, 3.1, 3.4, 4.1, 6.2, or the like. A device such as the one schematically illustrated in FIG. 1, which is discussed above, is optionally used to perform these assays. In these methods, the separation region typically includes an anion ion-exchange material, which effects separation of the net negatively charged phosphorylated reaction product from at least one other material (e.g., unphosphorylated reactants, kinases, etc.) based upon the difference in net charge of the reaction product and the at least one other material.

In one embodiment, the methods of performing a kinase assay optionally include flowing the kinase through a first channel fluidly coupled to a first source of the kinase into a mixing region in the microfluidic device. Thereafter, the kinase substrate is typically flowed through a second channel fluidly coupled to a first source of the kinase substrate and, in turn, contacting the kinase in the mixing region and producing the phosphorylated product. Optionally, the kinase reactions are performed prior to introducing reaction mixtures into microfluidic devices, e.g., through capillary elements that fluidly communicate with separation regions. Other variations that are optionally adapted to these kinase assays are described throughout this disclosure.

Phosphatase Assays

Phosphatases are enzymes (EC 3.1.3) that hydrolyze phosphoric monoester bonds, resulting in the removal of a phosphate group. They include protein phosphatases which are typically involved in the regulation of various protein activities, and numerous acid and alkaline phosphatases. Assorted sugar and polynucleotide phosphatases hydrolyze, e.g., the removal of phosphate groups from polynucleotide termini. For example, certain phosphatases are commonly used in various nucleic acid recombination protocols, e.g., to remove phosphate groups from the 5' ends of cleaved cloning vectors to prevent recircularization during ligation, or the like.

Many phosphatase catalyzed reactions which are optionally modeled according to the methods of the present invention are described in, e.g., Pagani et al. (2001) "5'-Nucleotidase in the detection of increased activity of the liver form of alkaline phosphatase in serum," *Clin Chem.* 47(11):2046–2048, Abe et al. (2001) "Extracellular matrix regulates induction of alkaline phosphatase expression by ascorbic acid in human fibroblasts," *J. Cell Physiol.* 189(2): 144–151, Dirnbach et al. (2001) "Mg$^{2+}$ binding to alkaline phosphatase correlates with slow changes in protein lability," *Biochemistry* 40(37): 11219–11226, Tiedtke et al. (1983) "Acid phosphatase associated with discharging secretory vesicles (mucocysts) of *Tetrahymena thermophila*," *Eur. J. Cell Biol.* 30(2):254–257, Luchter-Wasylewska (2001) "Cooperative kinetics of human prostatic acid phosphatase," *Biochim. Biophys. Acta.* 1548(2):257–264, Pierrugues et al. (2001) "Lipid phosphate phosphatases in *Arabidopsis*. Regulation of the AtLPP1 gene in response to stress," *J. Biol. Chem.* 276(23):20300–20308, Wang et al. (2001) "Protein phosphatase 1alpha-mediated stimulation of apoptosis is associated with dephosphorylation of the retinoblastoma protein," *Oncogene* 20(43):6111–6122, Tan et al. (2001) "Phosphorylation of a novel myosin binding subunit of protein phosphatase 1 reveals a conserved mechanism in the regulation of actin cytoskeleton," *J. Biol. Chem.* 276(24):21209–21216, Moore et al. (1985) "The involvement of glucose-6-phosphatase in mucilage secretion by root cap cells of *Zea mays*," *Ann. Bot. (Lond).* 56:139–142, Ichai et al. (2001) "Glucose 6-phosphate hydrolysis is activated by glucagon in a low temperature-sensitive manner," *J. Biol. Chem.* 276(30):28126–28133, and Ye et al. (1996) "Inducer expulsion and the occurrence of an HPr(Ser-P)-activated sugar-phosphate phosphatase in *Enterococcus faecalis* and *Streptococcus pyogenes*," *Microbiology* 142(Pt 3):585–592.

In certain embodiments, the phosphatase assays of the invention include flowing a phosphatase solution (e.g., a protein phosphatase, an acid phosphatase, an alkaline phosphatase, a polynucleotide phosphatase, or the like) and a phosphatase substrate solution into contact to produce a dephosphorylated product, and flowing at least the reaction product through a separation region of a microchannel in the microfluidic device under pressure. Optionally, the phosphatase reactions are performed prior to introducing reaction mixtures into microfluidic devices, e.g., through capillary elements that fluidly communicate with separation regions. A device such as the one schematically illustrated in FIG. 1, which is discussed above, is optionally used to perform these assays. In these methods, the separation region typically includes a cation ion-exchange material, which effects separation of the net positively charged dephosphorylated reaction product from at least one other material (e.g., phosphorylated reactants, phosphatases, etc.) based upon the difference in net charge of the reaction product and the at least one other material.

In one embodiment, the methods of performing a phosphatase assay optionally include flowing the phosphatase through a first channel fluidly coupled to a first source of the phosphatase into a mixing region in the microfluidic device. Thereafter, the phosphatase substrate is typically flowed through a second channel fluidly coupled to a first source of the phosphatase substrate and, in turn, contacting the phosphatase in the mixing region and producing the dephosphorylated product. Other variations that are optionally adapted to these phosphatase assays are described throughout this disclosure.

Microfluidic Devices

Many different microscale systems are optionally adapted for use in the chromatographic separation methods of the present invention. These systems are described in numerous publications by the inventors and their coworkers, including certain issued U.S. patents, such as U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, U.S. Pat. No. 5,959,291 (Morten J. Jensen) issued Sep. 28, 1999, U.S. Pat. No. 5,964,995 (Theo T. Nikiforov et al.) issued Oct. 12, 1999, U.S. Pat. No. 5,965,001 (Calvin Y. H. Chow et al.) issued Oct. 12, 1999, U.S. Pat. No. 5,965,410 (Calvin Y. H. Chow et al.) issued Oct. 12, 1999, U.S. Pat. No. 5,972,187 (J. Wallace Parce et al.) issued Oct. 26, 1999, U.S. Pat. No. 5,976,336 (Robert S. Dubrow et al.) issued Nov. 2, 1999, U.S. Pat. No. 5,989,402 (Calvin Y. H. Chow et al.) issued Nov. 23, 1999, U.S. Pat. No. 6,001,231 (Anne R. Kopf-Sill) issued Dec. 14, 1999, U.S. Pat. No. 6,011,252 (Morten J. Jensen) issued Jan. 4, 2000, U.S. Pat. No. 6,012,902 (J. Wallace Parce) issued Jan. 11, 2000, U.S. Pat. No. 6,042,709 (J. Wallace Parce et al.) issued Mar. 28, 2000, U.S. Pat. No. 6,042,710 (Robert S. Dubrow) issued Mar. 28, 2000, U.S. Pat. No. 6,046,056 (J. Wallace Parce et al.) issued Apr. 4, 2000, U.S. Pat. No. 6,048,498 (Colin B. Kennedy) issued Apr. 11, 2000, U.S. Pat. No. 6,068,752 (Robert S. Dubrow et al.) issued May 30, 2000, U.S. Pat. No. 6,071,478 (Calvin Y. H. Chow) issued Jun. 6, 2000, U.S. Pat. No. 6,074,725 (Colin B. Kennedy) issued Jun. 13, 2000, U.S. Pat. No. 6,080,295 (J. Wallace Parce et al.) issued Jun. 27, 2000, U.S. Pat. No. 6,086,740 (Colin B. Kennedy) issued Jul. 11, 2000, U.S. Pat. No. 6,086,825 (Steven A. Sundberg et al.) issued Jul. 11, 2000, U.S. Pat. No. 6,090,251 (Steven A. Sundberg et al.) issued Jul. 18, 2000, U.S. Pat. No. 6,100,541 (Robert Nagle et al.) issued Aug. 8, 2000, U.S. Pat. No. 6,107,044 (Theo T. Nikiforov) issued Aug. 22, 2000, U.S. Pat. No. 6,123,798 (Khushroo Gandhi et al.) issued Sep. 26, 2000, U.S. Pat. No. 6,129,826 (Theo T. Nikiforov et al.) issued Oct. 10, 2000, U.S. Pat. No. 6,132,685 (Joseph E. Kersco et al.) issued Oct. 17, 2000, U.S. Pat. No. 6,148,508 (Jeffrey A. Wolk) issued Nov. 21, 2000, U.S. Pat. No. 6,149,787 (Andrea W. Chow et al.) issued Nov. 21, 2000, U.S. Pat. No. 6,149,870 (J. Wallace Parce et al.) issued Nov. 21, 2000, U.S. Pat. No. 6,150,119 (Anne R. Kopf-Sill et al.) issued Nov. 21, 2000, U.S. Pat. No. 6,150,180 (J. Wallace Parce et al.) issued Nov. 21, 2000, U.S. Pat. No. 6,153,073 (Robert S. Dubrow et al.) issued Nov. 28, 2000, U.S. Pat. No. 6,156,181 (J. Wallace Parce et al.) issued Dec. 5, 2000, U.S. Pat. No. 6,167,910 (Calvin Y. H. Chow) issued Jan. 2, 2001, U.S. Pat. No. 6,171,067 (J. Wallace Parce) issued Jan. 9, 2001, U.S. Pat. No. 6,171,850 (Robert Nagle et al.) issued Jan. 9, 2001, U.S. Pat. No. 6,172,353 (Morten J. Jensen) issued Jan. 9, 2001, U.S. Pat. No. 6,174,675 (Calvin Y. H. Chow et al.) issued Jan. 16, 2001, U.S. Pat. No. 6,182,733 (Richard J. McReynolds) issued Feb. 6, 2001, U.S. Pat. No. 6,186,660 (Anne R. Kopf-Sill et al.) issued Feb. 13, 2001, U.S. Pat. No. 6,221,226 (Anne R. Kopf-Sill) issued Apr. 24, 2001, U.S. Pat. No. 6,233,048 (J. Wallace Parce) issued May 15, 2001, U.S. Pat. No. 6,235,175 (Robert S. Dubrow et al.) issued May 22, 2001, U.S. Pat. No. 6,235,471 (Michael Knapp et al.) issued May 22, 2001, U.S. Pat. No. 6,238,538 (J. Wallace Parce et al.) issued May 29, 2001, U.S. Pat. No. 6,251,343 (Robert S. Dubrow et al.) issued Jun. 26, 2001, U.S. Pat. No. 6,267,858 (J. Wallace Parce et al.) issued Jul. 31, 2001, U.S. Pat. No. 6,274,089 (Andrea W. Chow et al.) issued Aug. 14, 2001, U.S. Pat. No. 6,274,337 (J. Wallace Parce et al.) issued Aug. 14, 2001, U.S. Pat. No. 6,287,520 (J. Wallace Parce et al.) issued Sep. 11, 2001, U.S. Pat. No. 6,287,774 (Theo T. Nikiforov) issued Sep. 11, 2001, U.S. Pat. No. 6,303,343 (Anne R. Kopf-Sill) issued Oct. 16, 2001, U.S. Pat. No. 6,306,590 (Tammy Burd Mehta et al.) issued Oct. 23, 2001, and U.S. Pat. No. 6,306,659 (J. Wallace Parce et al.) issued Oct. 23, 2001.

Systems adapted for use with the devices of the present invention are also described in, e.g., various published PCT applications, including WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, WO 01/17797, and WO 01/27253.

The methods of the invention are generally performed within fluidic channels along which reagents, enzymes, samples, eluents, separation buffers, and other fluids are disposed and/or flowed. In some cases, as mentioned above, the channels are simply present in a capillary or pipettor element, e.g., a glass, fused silica, quartz or plastic capillary. The capillary element is fluidly coupled to a source of, e.g., the reagent, sample, modulator, or other solution (e.g., by dipping the capillary element into a well on a microtiter plate), which is then flowed along the channel (e.g., a microchannel) of the element. In preferred embodiments, the capillary element is integrated into the body structure of a microfluidic device. The term "microfluidic," as used herein, generally refers to one or more fluid passages, chambers or conduits which have at least one internal cross-sectional dimension, e.g., depth, width, length, diameter, etc., that is less than 500 µm, and typically between about 0.1 µm and about 500 µm.

In the devices of the present invention, the microscale channels or cavities typically have at least one cross-sectional dimension between about 0.1 µm and 200 µm, preferably between about 0.1 µm and 100 µm, and often between about 0.1 µm and 50 µm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "Y" and/or "T" intersections, or any number of other structures whereby two channels are in fluid communication.

The body structures of the microfluidic devices described herein are typically manufactured from two or more separate portions or substrates which when appropriately mated or joined together, form the microfluidic device of the invention, e.g., containing the channels and/or chambers described herein. During body structure fabrication, the microfluidic devices described herein will typically include a top portion, a bottom portion, and an interior portion, wherein the interior portion substantially defines the channels and chambers of the device. As mentioned, at least the separation region(s) of the devices of the present invention are optionally fabricated to include a chromatographic material (e.g., an anion exchange material, a cation exchange material, a hydrophobic exchange material, a hydrophilic exchange material, or the like) integral with and exposed on the inner surface of at least a portion of the microchannel(s) that include the separation region(s). Alternatively, as noted above, chromatographic materials are optionally flowed into the relevant portions of the device during device operation.

In one aspect, a bottom portion of the unfinished device includes a solid substrate that is substantially planar in structure, and which has at least one substantially flat upper surface. Channels are typically fabricated on one surface of the device and sealed by overlaying the channels with an upper substrate layer. A variety of substrate materials are optionally employed as the upper or bottom portion of the device. Typically, because the devices are microfabricated, substrate materials will be selected based upon their compatibility with known microfabrication techniques, e.g., photolithography, wet chemical etching, laser ablation, air abrasion techniques, LIGA, reactive ion etching, injection molding, embossing, and other techniques. The substrate materials are also generally selected for their compatibility with the full range of conditions to which the microfluidic devices may be exposed, including extremes of pH, temperature, electrolyte concentration, and/or for their chromatographic properties. Accordingly, in some preferred aspects, the substrate material may include materials normally associated with the semiconductor industry in which such microfabrication techniques are regularly employed, including, e.g., silica-based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. In preferred embodiments, at least the separation region(s) is/are fabricated from polyacrylamide, dimethylacrylamide, modified versions thereof, nonionic detergents, ionic detergents, or the like. Such polymeric substrates are readily manufactured using available microfabrication techniques, as described above, or from microfabricated masters, using known molding techniques, such as injection molding, embossing or stamping, or by polymerizing the polymeric precursor material within the mold (See, e.g., U.S. Pat. No. 5,512,131). Such polymeric substrate materials are preferred for their ease of manufacture, low cost and disposability, as well as their general inertness to most extreme reaction conditions. Again, these polymeric materials optionally include treated surfaces, e.g., derivatized or coated surfaces, to enhance their utility in the microfluidic system, e.g., to provide enhanced fluid direction, e.g., as described in U.S. Pat. No. 5,885,470 (J. Wallace Parce et al.) issued Mar. 23, 1999, and which is incorporated herein by reference in its entirety for all purposes.

The channels and/or cavities of the microfluidic devices are typically fabricated into the upper surface of the bottom substrate or portion of the device, as microscale grooves or indentations, using the above described microfabrication techniques. The top portion or substrate also comprises a first planar surface, and a second surface opposite the first planar surface. In the microfluidic devices prepared in accordance with certain aspects of the methods described herein, the top portion can include at least one aperture, hole or port disposed therethrough, e.g., from the first planar surface to the second surface opposite the first planar surface. In other embodiments, the port(s) are optionally omitted, e.g., where fluids are introduced solely through external capillary elements.

The first planar surface of the top portion or substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. Bonding of substrates is typically carried out by any of a number of different methods, e.g., thermal bonding, solvent bonding, ultrasonic welding, and the like. The finished body structure of a device is a unitary structure that houses, e.g., the channels and/or chambers of the device.

The hole(s) in the top of the finished device is/are oriented to fluidly communicate with at least one of the channels and/or cavities. In the completed device, the hole(s) optionally function as reservoirs for facilitating fluid or material introduction into the channels or chambers of the device, as well as providing ports at which, e.g., pressure elements (e.g., vacuum sources, etc.) are optionally placed into contact with fluids within the device, allowing application of pressure gradients along the channels of the device to control and direct fluid transport within the device. In optional embodiments, extensions are provided over these reservoirs to allow for increased fluid volumes, permitting longer running assays, and better controlling fluid flow parameters, e.g., hydrostatic pressures. Examples of methods and apparatuses for providing such extensions are described in U.S. application Ser. No. 09/028,965, filed Feb. 24, 1998, and incorporated herein by reference. These devices are optionally coupled to a sample introduction port, e.g., a pipettor or capillary element, which serially introduces multiple samples, e.g., from the wells of a microtiter plate. Thus, in some embodiments, both reservoirs in the upper surface and external capillary elements are present in a single device.

The sources of reagents, enzymes, substrates, samples, eluents, separation buffers, and other materials are optionally fluidly coupled to the microchannels in any of a variety of ways. In particular, those systems comprising sources of materials set forth in Knapp et al. "Closed Loop Biochemical Analyzers" (WO 98/45481; PCT/US98/06723) and U.S. Pat. No. 5,942,443 issued Aug. 24, 1999, entitled "High Throughput Screening Assay Systems in Microscale Fluidic Devices" to J. Wallace Parce et al. and, e.g., in 60/128,643 filed Apr. 4, 1999, entitled "Manipulation of Microparticles In Microfluidic Systems," by Mehta et al. are applicable.

In these systems and as noted above, a capillary or pipettor element (i.e., an element in which components are optionally moved from a source to a microscale element such as a second channel or reservoir) is temporarily or permanently coupled to a source of material. The source is optionally internal or external to a microfluidic device that includes the pipettor or capillary element. Example sources include microwell plates, membranes or other solid substrates comprising lyophilized components, wells or reservoirs in the body of the microscale device itself and others.

Flow of Materials in Microfluidic Systems

A preferred method of flowing materials along the microchannels or other cavities of the devices described herein is by pressure-based flow. Pressure is applied with or without a simultaneously applied electric field. Application of a pressure differential along a channel is carried out by any of a number of approaches. For example, it may be desirable to provide relatively precise control of the flow rate of materials, e.g., to precisely control incubation or separation times, etc. As such, in many preferred aspects, flow systems that are more active than hydrostatic pressure driven systems are employed. In certain cases, reagents may be flowed by applying a pressure differential across the length of the analysis channel. For example, a pressure source (positive or negative) is applied at the reagent reservoir at one end of the analysis channel, and the applied pressure forces the reagents through the channel. The pressure source is optionally pneumatic, e.g., a pressurized gas, or a positive displacement mechanism, i.e., a plunger fitted into a reagent reservoir, for forcing the reagents through the analysis channel. Alternatively, a vacuum source is applied to a reservoir at the opposite end of the channel to draw the reagents through the channel. See, FIG. 1. Pressure or vacuum sources may be supplied external to the device or system, e.g., external vacuum or pressure pumps sealably fitted to the inlet or outlet of the analysis channel, or they may be internal to the device, e.g., microfabricated pumps integrated into the device and operably linked to the analysis channel. Examples of microfabricated pumps have been widely described in the art. See, e.g., published International Application No. WO 97/02357.

In an alternative simple passive aspect, the reagents are deposited in a reservoir or well at one end of an analysis channel and at a sufficient volume or depth, that the reagent sample creates a hydrostatic pressure differential along the length of the analysis channel, e.g., by virtue of it having greater depth than a reservoir at an opposite terminus of the channel. The hydrostatic pressure then causes the reagents to flow along the length of the channel. Typically, the reservoir volume is quite large in comparison to the volume or flow through rate of the channel, e.g., 10 µl reservoirs, vs. 1000 µm$^2$ channel cross-section. As such, over the time course of the assay/separation, the flow rate of the reagents will remain substantially constant, as the volume of the reservoir, and thus, the hydrostatic pressure changes very slowly. Applied pressure is then readily varied to yield different reagent flow rates through the channel. In screening applications, varying the flow rate of the reagents is optionally used to vary the incubation time of the reagents. In particular, by slowing the flow rate along the channel, one can effectively lengthen the amount of time between introduction of reagents and detection of a particular effect. Alternatively, analysis channel lengths, detection points, or reagent introduction points are varied in fabrication of the devices, to vary incubation times. See also, "Multiport Pressure Control System," by Chien and Parce, U.S. Ser. No. 60/184,390, filed Feb. 23, 2000, which describes multiport pressure controllers that couple pumps to multiple device reservoirs.

In further alternate aspects, hydrostatic, wicking and capillary forces are additionally, or alternately, used to provide for fluid flow. See, e.g., "Method and Apparatus for Continuous Liquid Flow in Microscale Channels Using Pressure Injection, Wicking and Electrokinetic Injection," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

In alternative aspects, flow of reagents is driven by inertial forces. In particular, the analysis channel is optionally disposed in a substrate that has the conformation of a rotor, with the analysis channel extending radially outward from the center of the rotor. The reagents are deposited in a reservoir that is located at the interior portion of the rotor and is fluidly connected to the channel. During rotation of the rotor, the centripetal force on the reagents forces the reagents through the analysis channel, outward toward the edge of the rotor. Multiple analysis channels are optionally provided in the rotor to perform multiple different analyses. Detection of a detectable signal produced by the reagents is then carried out by placing a detector under the spinning rotor and detecting the signal as the analysis channel passes over the detector. Examples of rotor systems have been previously described for performing a number of different assay types. See, e.g., Published International Application No. WO 95/02189. Test compound reservoirs are optionally provided in the rotor, in fluid communication with the analysis channel, such that the rotation of the rotor also forces the test compounds into the analysis channel.

For purposes of illustration, the discussion has focused on a single channel and accessing capillary; however, it will be readily appreciated that these aspects may be provided as multiple parallel analysis channels (e.g., each including mixing and separation regions) and accessing capillaries, in order to substantially increase the throughput of the system. Specifically, single body structures may be provided with multiple parallel analysis channels coupled to multiple sample accessing capillaries that are positioned to sample multiple samples at a time from sample libraries, e.g., multiwell plates. As such, these capillaries are generally spaced at regular distances that correspond with the spacing of wells in multiwell plates, e.g., 9 mm centers for 96 well plates, 4.5 mm for 384 well plates, and 2.25 mm for 1536 well plates.

In alternate aspects, an applied pressure is accompanied by the simultaneous application of an electric field to further effect fluid transport, e.g., through the mixing and/or separation regions of the microchannel. The electrokinetic transport systems of the invention typically utilize electric fields applied along the length of microchannels that have a surface potential or charge associated therewith. When fluid is introduced into the microchannel, the charged groups on the inner surface of the microchannel ionize, creating locally concentrated levels of ions near the fluid surface interface. Under an electric field, this charged sheath migrates toward the cathode or anode (depending upon whether the sheath comprises positive or negative ions) and pulls the encompassed fluid along with it, resulting in bulk fluid flow. This flow of fluid is generally termed electroosmotic flow. Where the fluid includes reagents (e.g., materials to be separated), the reagents are also pulled along. A more detailed description of controlled electrokinetic material transport systems in microfluidic systems is described in published International Patent Application No. WO 96/04547, which is incorporated herein by reference.

Integrated Systems

The present invention also relates to a device or integrated system which is typically used to perform high-throughput assays and chromatographic separations as described herein. The system includes a body structure that has at least two intersecting microchannels fabricated therein and a source of a first chromatographic material coupled to at least one of the at least two channels. The system also includes a pressure source for applying positive or negative pressure to at least one of the two intersecting channels and a controller. The controller optionally dispenses a first aliquot of the first chromatographic material into at least a first of the at least two intersecting channels. The device or system includes flowing materials in the microfluidic device in the absence of an applied electric field, or alternatively, flowing materials in the microfluidic device under a simultaneously applied electric field.

In certain embodiments, the system includes a first source of a first material and a second source of a second material, in which, during operation of the device, the first and second material are flowed into a mixing region in at least one of the at least two intersecting channels. Optionally, the first or second source is present in a microtiter dish. In this embodiment, the microfluidic device also includes an external capillary element that samples the first or second material from the microtiter dish. For example, during operation of the device, the external capillary element optionally draws fluid into the microfluidic device by applying negative pressure at the source of the first or second material. The device also optionally includes a reservoir on an upper surface of the device that includes a source of the first or second material.

The intersecting channels of the device or integrated system of the invention typically include a mixing region and a separation region. The source of the chromatographic material is optionally fluidly coupled to the separation region, and the controller, during operation of the device, typically flows aliquots of chromatographic material into the separation region. The controller also optionally directs flow of first and second materials from sources of the first and the second materials into the mixing region in which the first and second materials are mixed. Additionally, the first or second materials, or products thereof, are flowed into the separation region in which the first or second material or the reaction products resulting from the mixing are separated from each other or from additional materials, based upon a difference in, e.g., net charge or another distinguishing property (e.g., a polarity, a polarizablity, a binding affinity, a hydrophobic property, a hydrophilic property, an amphiphilic property, an electrostatic property, or the like) of the first or second material or the reaction products or the additional materials. The first or second material or the reaction product(s) optionally include, e.g., a biological molecule, an artificial molecule, an ion, a polar molecule, an apolar molecule, an antibody, an antigen, an inorganic molecule, an organic molecule, a drug, a receptor, a ligand, a neurotransmitter, a cytokine, a chemokine, a hormone, a particle, a bead, a functionalized bead, a liposome, a cell, a nucleic acid, DNA, RNA, an oligonucleotide, a ribozyme, a protein, a phosphoprotein, a glycoprotein, a lipoprotein, a peptide, a phosphopeptide, a glycopeptide, a lipopeptide, an enzyme, an enzyme substrate, a carbohydrate, a lipid, a label, a dye, a fluorophore, or the like.

As described above, the chromatographic material of the device or integrated system typically includes an ion exchange material, a hydrophobic adsorbent material, a hydrophilic adsorbent material, an affinity adsorbent material, a metal chelating adsorbent material, an amphiphilic adsorbent material, an electrostatic adsorbent material, a chemisorbent, an immobilized enzyme, an immobilized receptor, an immobilized antibody, an immobilized antigen, or the like. For example, an inner surface of at least one of the microchannels optionally includes the chromatographic material, or the chromatographic material is optionally coated on an inner surface of at least one of the microchannels. An appropriate chromatographic material includes, e.g., a polyarginine, a polylysine, a modified polyacrylamide, a modified dimethylacrylamide, a nonionic detergent, or the like. A polyacrylamide or a dimethylacrylamide for use as a chromatographic material is optionally modified (e.g., via covalent attachment, via adsorption, or the like) by anionic or cationic additives.

In certain embodiments, the device or integrated system includes a source of at least a second chromatographic material in which the source is fluidly coupled to at least one of the at least two intersecting microchannels. Alternatively, the chromatographic material is stored in a reservoir, which reservoir is fluidly coupled to a separation region located in at least one of the at least two intersecting microchannels. The device or integrated system of the present invention also typically includes a detector mounted proximal to a detection region of the microfluidic device in which the detection region is within or fluidly coupled to at least one of the at least two intersecting microchannels.

The present invention, in addition to other integrated system components, also optionally includes a microfluidic device handler for performing the methods disclosed herein. Specifically, the microfluidic device handler includes a holder configured to receive the microfluidic device, a container sampling region proximal to the holder, and the controller. During operation of the handler, the controller directs, e.g., dipping of microfluidic device capillary or pipettor element(s) into a portion of, e.g., a microwell plate in the container sampling region. The microfluidic device handler also optionally includes a computer or a computer readable medium operably connected to the controller. The computer or the computer readable medium typically includes an instruction set for varying or selecting a rate or a mode of dipping capillary element(s) into fluid materials.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations in addition to the operations specifically described herein. Aside from fluid handling, assays, and separation of sample and/or reaction components, other upstream or downstream operations include, e.g., extraction, purification, amplification, cellular activation, labeling reactions, dilution, aliquotting, labeling of components, assays and detection operations, electrokinetic or pressure-based injection of components or materials into contact with one another, or the like. Assay and detection operations include, without limitation, cell fluorescence assays, cell activity assays, receptor/ligand assays, immunoassays, or the like.

In the present invention, the separated materials are optionally monitored and/or detected so that, e.g., an activity can be determined. The systems described herein generally include microfluidic device handlers, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

The controllers of the integrated systems of the present invention direct dipping of capillary elements into, e.g., microwell plates to sample reagents, such as enzymes and substrates, fluid recirculation baths or troughs, or the like. A variety of controlling instrumentation is also optionally utilized in conjunction with the microfluidic devices and handling systems described herein, for controlling the transport, concentration, direction, and motion of fluids and/or separation of materials within the devices of the present invention, e.g., by pressure-based control.

As described above, in many cases, fluid transport, concentration, and direction are controlled in whole or in part, using pressure based flow systems that incorporate external or internal pressure sources to drive fluid flow. Internal sources include microfabricated pumps, e.g., diaphragm pumps, thermal pumps, and the like that have been described in the art. See, e.g., U.S. Pat. Nos. 5,271,724, 5,277,556, and 5,375,979 and Published PCT Application Nos. WO 94/05414 and WO 97/02357. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port (see, FIG. 1) and configuring the various channels with appropriate resistance to yield desired flow rates. Example systems are also described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices described herein optionally include signal detectors, e.g., which detect concentration, fluorescence, phosphorescence, radioactivity, pH, charge, absorbance, refractive index, luminescence, temperature, magnetism, mass (e.g., mass spectrometry), or the like. The detector(s) optionally monitors one or a plurality of signals from upstream and/or downstream (e.g., in or proximal to the separation region) of an assay mixing point in which, e.g., a ligand and an enzyme are mixed. For example, the detector optionally monitors a plurality of optical signals which correspond in position to "real time" assay/separation results.

Example detectors or sensors include photomultiplier tubes, CCD arrays, optical sensors, temperature sensors, pressure sensors, pH sensors, conductivity sensors, mass sensors, scanning detectors, or the like. Materials which emit a detectable signal are optionally flowed past the detector, or, alternatively, the detector can move relative to the array to determine the position of an assay component (or, the detector can simultaneously monitor a number of spatial positions corresponding to channel regions, e.g., as in a CCD array). Each of these types of sensors is optionally readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. The detector optionally includes or is operably linked to a computer, e.g., which has software for converting detector signal information into assay result information (e.g., kinetic data of modulator activity), or the like. A microfluidic system optionally employs multiple different detection systems for monitoring the output of the system. Detection systems of the present invention are used to detect and monitor the materials in a particular channel region (or other reaction detection region).

The detector optionally exists as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector, and the computer.

Computer

As noted above, the microfluidic devices and integrated systems of the present invention optionally include a computer operably connected to the controller. The computer typically includes an instruction set, e.g., for varying or selecting a rate or a mode of dipping capillary or pipettor elements into fluid materials, for sampling fluidic materials (e.g., enzymes, substrates, reactants, chromatographic materials, eluents, separation buffers, etc.), or the like. Additionally, either or both of the controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation, e.g., varying or selecting the rate or mode of fluid and/or microfluidic device movement, controlling flow rates within microscale channels, directing xyz translation of the microfluidic device or of one or more microwell plates, or the like. The computer then receives the data from the one or more sensors/detectors included within the system, and interprets the data, either provides it in a user understood format, or uses that data to initiate further controller instructions, in accordance with the programming, e.g., such as in monitoring and control of flow rates, applied voltages, and the like. Additionally, the software is optionally used to control, e.g., pressure or electrokinetic modulated injection or withdrawal of material.

Example Integrated System

Figure 2:
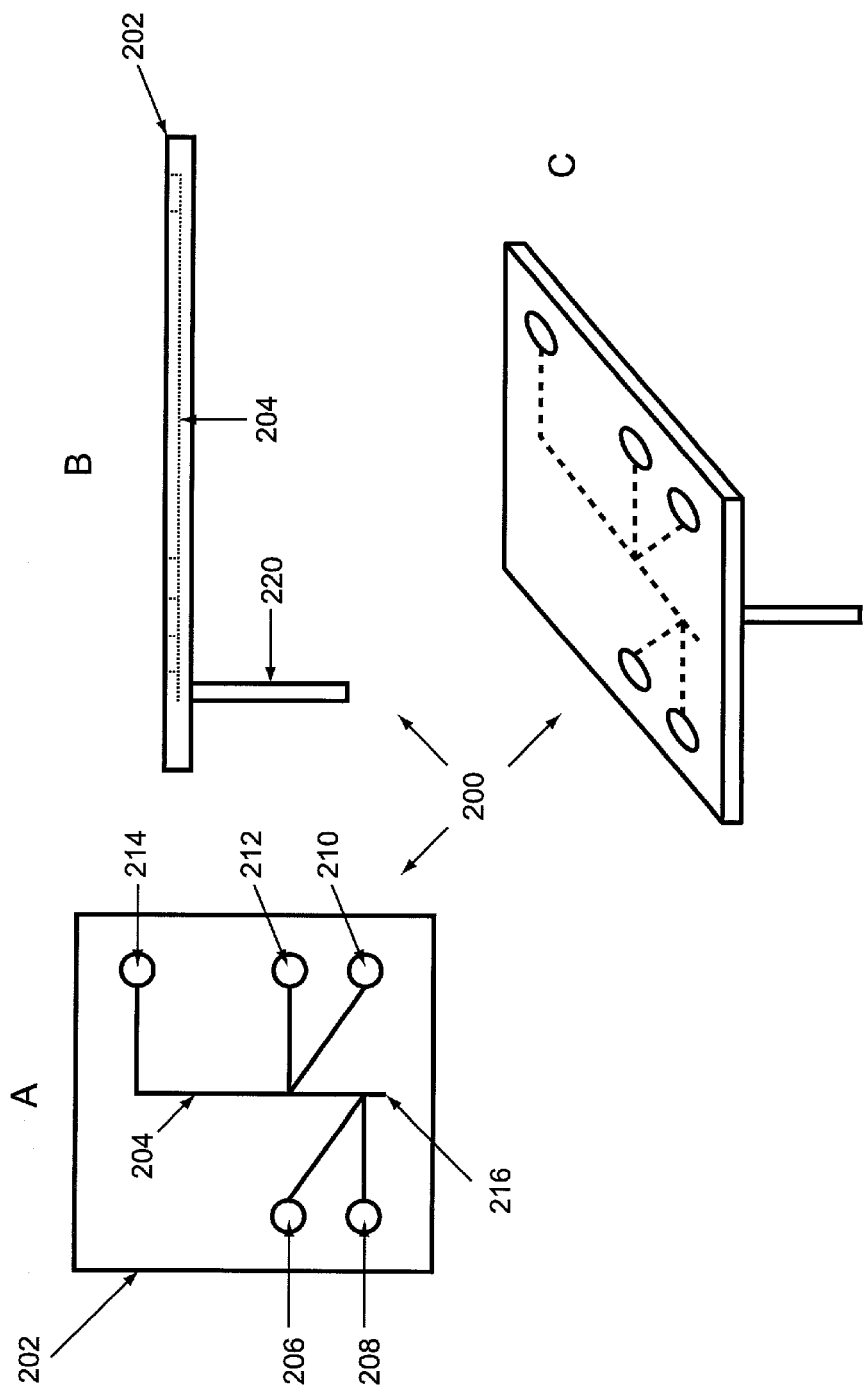
FIGS. 2A–2C schematically show a microfluidic device that includes a capillary element from various viewpoints.
Figure 3:
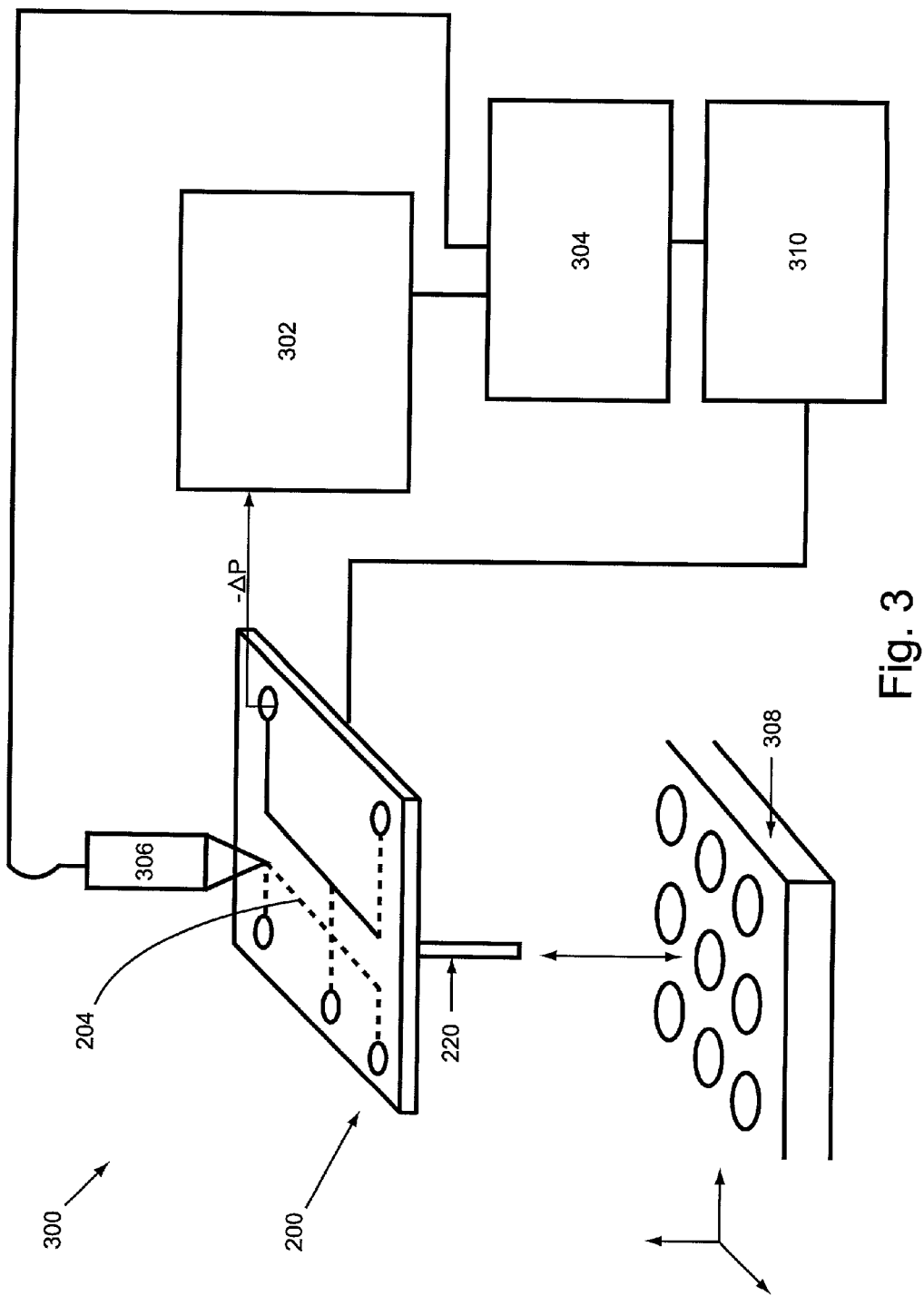
FIG. 3 schematically illustrates a integrated system that includes the microfluidic device of FIGS. 2A–2C.

FIG. 2, Panels A, B, and C and FIG. 3 provide additional details regarding example integrated systems that are optionally used to practice the methods herein. As shown, body structure 202 of microfluidic device 200 has main microchannel 204 disposed therein. For example, at least main microchannel 204 optionally includes a chromatographic material (e.g., coating, or as an integral component of, an inner surface) in a separation region. As described herein, aliquots of chromatographic material are also optionally flowed into, e.g., main microchannel 204 from other device cavities. A sample, chromatographic material, or other material is optionally flowed from pipettor or capillary element 220 towards reservoir 214, e.g., by applying a vacuum at reservoir 214 (or another point in the system) and/or by applying appropriate voltage gradients. Alternatively, a vacuum is applied at reservoirs 208, 212 or through pipettor or capillary element 220. Additional materials, such as buffer solutions, substrate solutions, enzyme solutions, and the like, as described above are optionally flowed from wells 208 or 212 and into main microchannel 204. Flow from these wells is optionally performed by modulating fluid pressure, or by electrokinetic approaches as described (or both). Pressure-based flow is preferred. As fluid is added to main microchannel 204, e.g., from reservoir 208, the flow rate increases. The flow rate is optionally reduced by flowing a portion of the fluid from main microchannel 204 into flow reduction microchannel 206 or 210. The arrangement of channels depicted in FIG. 2 is only one possible arrangement out of many which are appropriate and available for use in the present invention. One alternative is schematically depicted in FIG. 1. Additional alternatives can be devised, e.g., by combining the microfluidic elements described herein, e.g., mixing regions, separation regions, or the like, with other microfluidic device components described in the patents and applications referenced herein.

Samples, chromatographic materials, and other materials are optionally flowed from the enumerated wells or from a source external to the body structure. As depicted, the integrated system optionally includes pipettor or capillary element 220, e.g., protruding from body 202, for accessing a source of materials external to the microfluidic system. Typically, the external source is a microtiter dish or other convenient storage medium. For example, as depicted in FIG. 3, pipettor or capillary element 220 can access microwell plate 308, which includes chromatographic materials, sample materials, buffers, substrate solutions, enzyme solutions, or the like, in the wells of the plate.

Detector 306 is in sensory communication with main microchannel 204, detecting signals resulting, e.g., from labeled materials flowing through the detection region. Detector 306 is optionally coupled to any of the channels or regions of the device where detection is desired. Detector 306 is operably linked to computer 304, which digitizes, stores, and manipulates signal information detected by detector 306, e.g., using any instruction set, e.g., for determining concentration, molecular weight or identity, or the like.

Fluid direction system 302 controls pressure, voltage, or both, e.g., at the wells of the system or through the channels of the system, or at vacuum couplings fluidly coupled to main microchannel 204 or other channels described above. Optionally, as depicted, computer 304 controls fluid direction system 302. In one set of embodiments, computer 304 uses signal information to select further parameters for the microfluidic system. For example, upon detecting the presence of a component of interest (e.g., following separation) in a sample from microwell plate 308, the computer optionally directs addition of a potential modulator of the component of interest into the system. In certain embodiments, controller 310 dispenses aliquots of chromatographic material into, e.g., main microchannel 204. In these embodiments, controller 310 is also typically operably connected to computer 304, which directs controller 310 function.

Although not shown, a microfluidic device handler is also typically included in the integrated systems of the present invention. Microfluidic device handlers generally control, e.g., the xyz translation of microfluidic device 200 relative to microwell plate 308, or other system components, under the direction of computer 304 to which device handlers are typically operably connected.

EXAMPLES

The following examples serves to illustrate, but not to limit the present invention.

Example 1

Protein a Kinase Assay Separation

Figure 4:
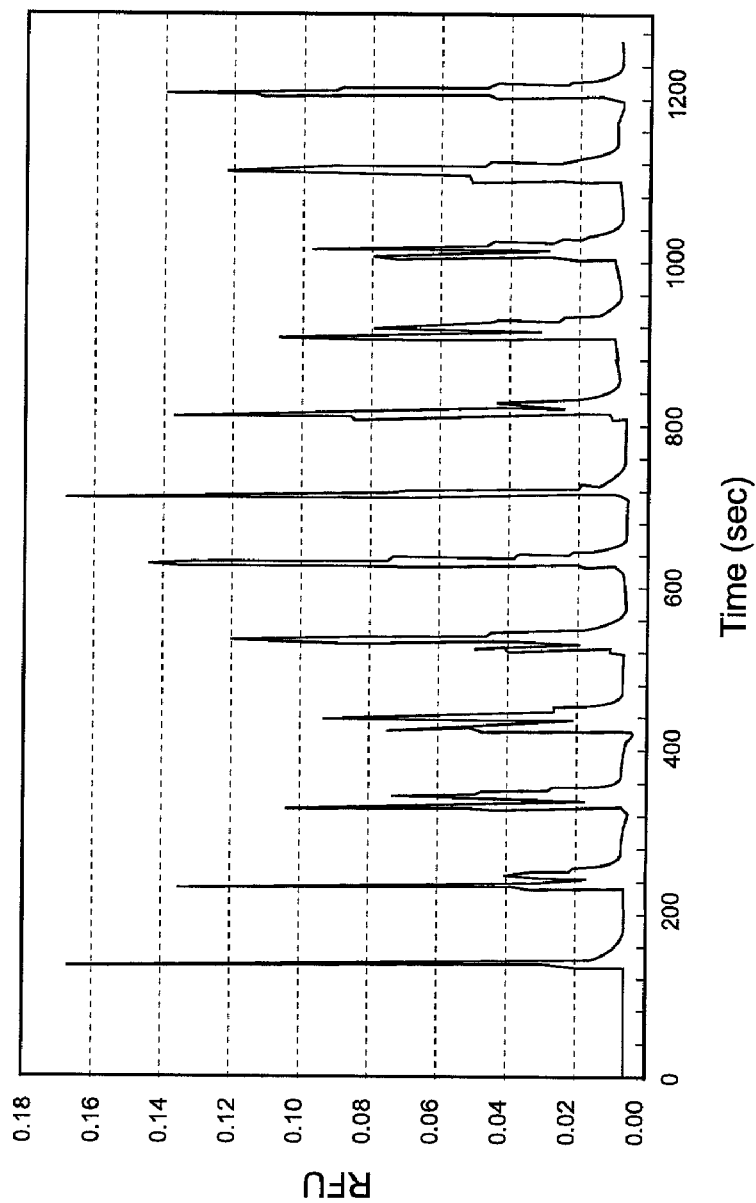
FIG. 4 is a data graph that illustrates the separation of two fluorescently labeled peptides.

FIG. 4 is a data graph that illustrates protein kinase A assay separations of two fluorescently labeled peptides, Fl-LRRASLG (net charge zero) and its phosphorylated analog, Fl-LRRA(pS)LG (net charge minus 2), by ion exchange in a microfluidic device modified by adsorption of polyarginine (pARG) (2 µM, 50 mM HEPES pH 7.5, 50 mM NaCl) onto a polydimethylacrylamide (pDMA) coating. Injections of various mixtures of these two peptides were made from a microtiter plate via capillary elements, and transport of the fluidic material through the channels of the device was by the application of vacuum to port of the device.

Example 2

Phospholipid Separation

Figure 5:
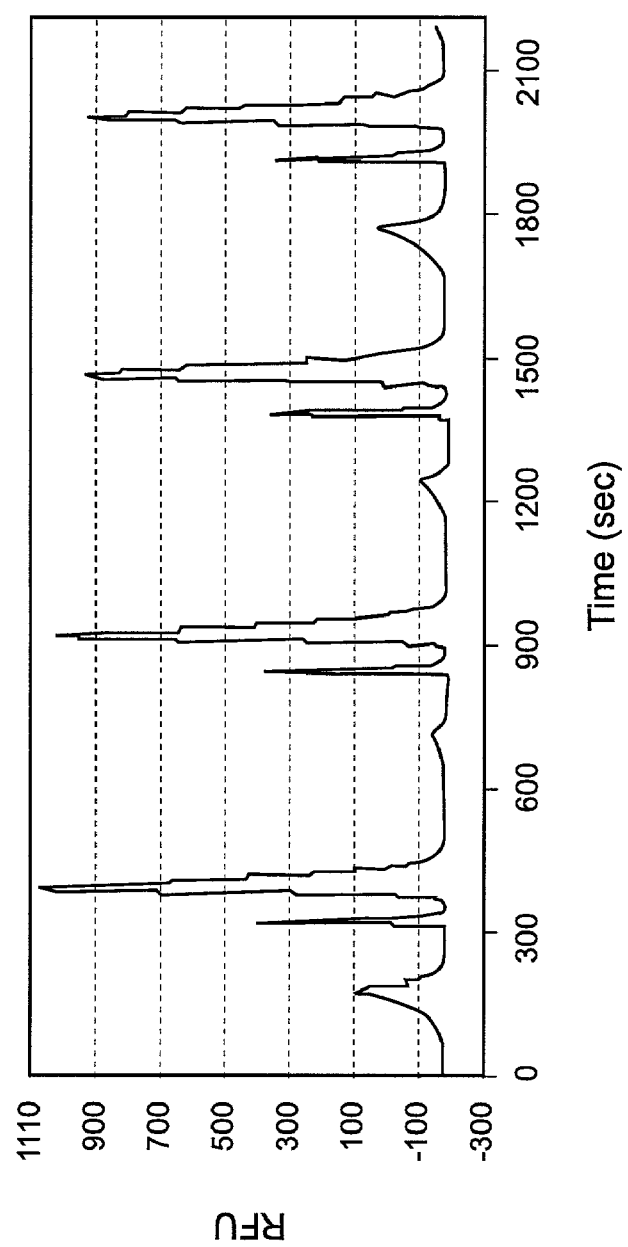
FIG. 5 is a data graph that illustrates the separation of fluorescently labeled phosphatidylcholine and phosphatidic acid by affinity chromatography.

FIG. 5 is a data graph that illustrates the separation of two fluorescently labeled phospholipids. Specifically, phosphatidylcholine (PC, net charge: zero) and phosphatidic acid (PA, net charge: −1) were separated by affinity chromatography performed in a microfluidic device similar to the one schematically depicted in FIG. 1. The separation region of the device was coated with Triton X-100™ prior to injecting the mixtures of PC and PA which were present in a molar ratio of 10:1 (i.e., PC:PA).

Example 3

Substrate/Product Separation

Figure 6:
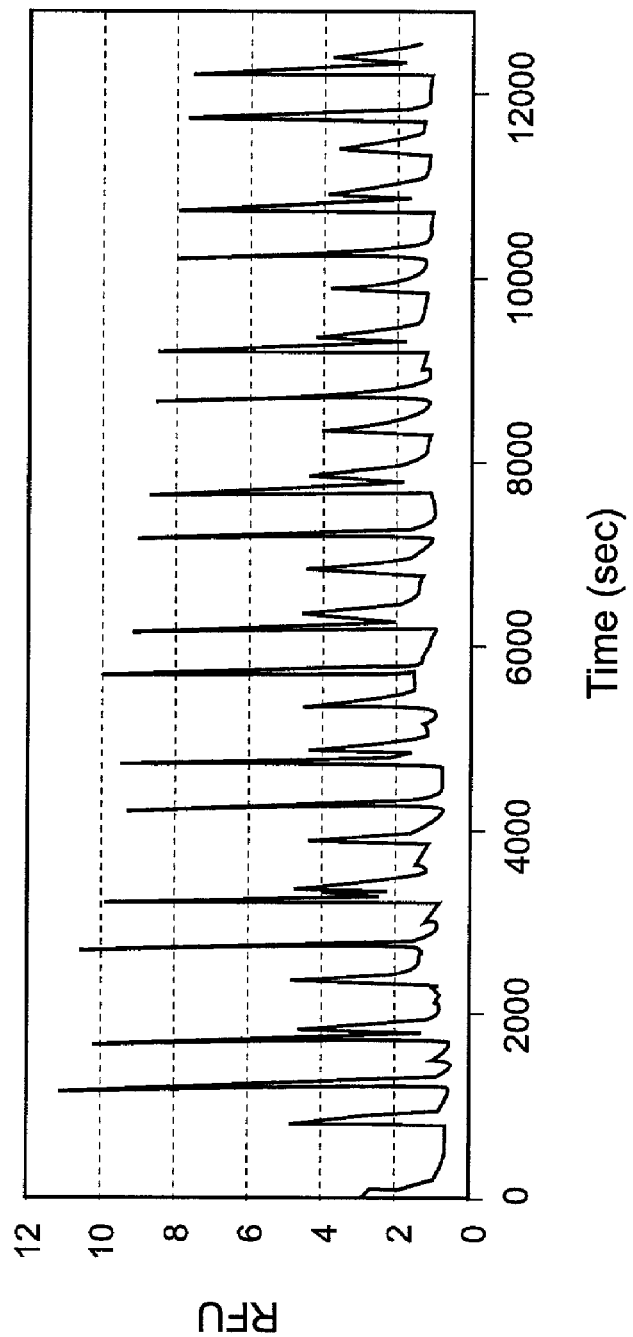
FIG. 6 is a data graph that illustrates the separation of fluorescently labeled BODIPY-ceramide and BODIPY-IPC by affinity chromatography.

FIG. 6 is a data graph that illustrates the separation of a fluorescently labeled substrate, BODIPY-ceramide (S, net charge: zero) and a fluorescently labeled product, BODIPY-IPC(P, net charge: −1) by affinity chromatography performed in a microfluidic device. The experiment involved consecutively injecting the substrate, the product, and a mixture of the substrate and product from a microtiter plate through a capillary element. Fluid transport was accomplished by applying a vacuum to one of the ports on the device. Note, that although the simultaneous application of an electric field is not essential, as illustrated below with respect to FIG. 7, it does accelerate separation times.

Example 4

Figure 7:
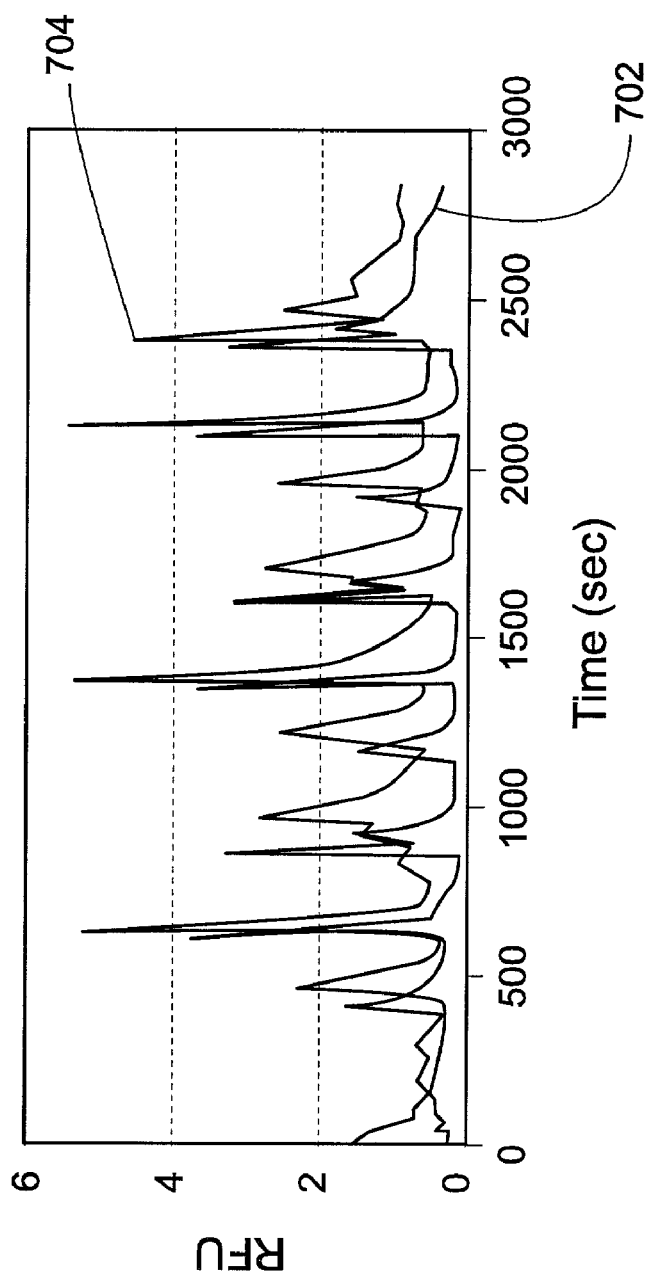
FIG. 7 is a data graph that illustrates separations of fluorescently labeled BODIPY-ceramide and BODIPY-IPC by affinity chromatography with and without an applied electric field.

Comparison of Substrate/Product Separations with and without the Simultaneous Application of an Electric Field FIG. 7 is a data graph that illustrates separations of a fluorescently labeled substrate, BODIPY-ceramide (S, net charge: zero) and a fluorescently labeled product, BODIPY-IPC(P, net charge: −1) by affinity chromatography performed in a microfluidic device with and without the simultaneous application of an electric field. Similar to Example 3, described above, the experiment involved consecutively injecting the substrate, the product, and a mixture of the substrate and product from a microtiter plate through a capillary element. A vacuum was applied to one of the ports on the device whether an electric field was applied or not. First trace 702 shows separations accomplished under the simultaneously applied electric field, while second trace 704 shows separations achieved in the absence of an applied electric field. As shown, separations performed with the application of an electric field were faster than those performed in the absence of an applied electric field. Thus, in one embodiment, the systems of the present invention include simultaneous application of pressure and an electric field to achieve separation.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of performing a mobility shift assay in a microfluidic device, the method comprising:
   flowing a reaction mixture comprising an enzyme, an enzyme substrate, and a product through a separation region of the microfluidic device under an applied pressure, which separation region comprises at least one ion-exchange material comprising a polyacrylamide material or a dimethylacrylamide material modified by one or more additives having formula (I), or:

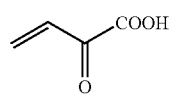

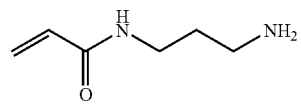

to separate the product from at least one other material based upon a net charge difference between the product and the at least one other material to produce separated materials; and,
   detecting at least one of the separated materials, thereby performing the mobility shift assay in the microfluidic device.

2. The method of claim 1, wherein the at least one other material comprises the enzyme and/or unreacted enzyme substrate.

3. The method of claim 1, wherein at least the separated materials are flowed in the microfluidic device in an absence of an applied electric field.

4. The method of claim 1, wherein at least the separated materials are flowed in the microfluidic device under at least one simultaneously applied electric field.

5. The method of claim 1, wherein one or more of the separated materials comprise a label.

6. The method of claim 1, wherein a microchannel comprises the separation region.

7. The method of claim 1, wherein the applied pressure is produced by a vacuum pump operably connected to the microfluidic device through a port that fluidly communicates with the separation region.

8. The method of claim 1, wherein the detecting step comprises at least an optical, a spectroscopic, a fluorescent, a mass, or a luminescent detection.

9. The method of claim 1, wherein a plurality of microbeads or a gel comprises the ion-exchange material.

10. The method of claim 1, wherein an inner surface of the separation region comprises the ion-exchange material.

11. The method of claim 1, wherein the ion-exchange material is coated on an inner surface of the separation region.

12. The method of claim 1, further comprising sampling the reaction mixture from a source external to the microfluidic device.

13. The method of claim 1, wherein the enzyme comprises a kinase, the enzyme substrate comprises a kinase substrate, and the product comprises a phosphorylated product.

14. The method of claim 13, wherein the kinase comprises a protein kinase, a protein kinase A, a protein kinase B, a protein kinase C, a hexokinase, a phosphofructokinase, a phosphoglycerate kinase, a pyruvate kinase, a cyclic AMP-dependent protein kinase, a cyclic GMP-dependent protein kinase, a calmodulin-dependent protein kinase II, a casein kinase I, a casein kinase II, a glycogen synthase kinase-3, a cyclin-dependent kinase, a p34/cdc2 kinase, or a nucleic acid kinase.

15. The method of claim 1, wherein the enzyme comprises a phosphatase, the enzyme substrate comprises a phosphatase substrate, and the product comprises a dephosphorylated product.

16. The method of claim 15, wherein the phosphatase comprises a protein phosphatase, an acid phosphatase, an alkaline phosphatase, a sugar phosphatase, or a polynucleotide phosphatase.

17. The method of claim 1, wherein prior to the flowing step, the method comprises:
flowing at least the enzyme through a first channel in fluid communication with an enzyme source into a mixing region of the microfluidic device; and,
flowing at least the enzyme substrate through a second channel in fluid communication with an enzyme substrate source into the mixing region, wherein the enzyme converts at least some of the enzyme substrate to the product, thereby producing the reaction mixture.

18. The method of claim 17, wherein a microchannel comprises the mixing region.

19. The method of claim 1, the method further comprising flowing the ion-exchange material into the separation region.

20. The method of claim 19, wherein the flowed ion-exchange material coats an inner surface of the separation region.

21. The method of claim 19, comprising continuously flowing the ion-exchange material into the separation region for a selected period of time.

22. The method of claim 19, comprising flowing multiple aliquots of the ion-exchange material into the separation region.

23. The method of claim 19, wherein the ion-exchange material is stored in a reservoir, which reservoir is in fluid communication with the separation region.

24. The method of claim 19, further comprising flowing one or more other chromatographic materials or surface coatings into the separation region.

25. The method of claim 24, further comprising flowing the ion-exchange material and the other chromatographic materials or surface coatings sequentially into the separation region.

26. The method of claim 25, wherein each sequentially flowed material or surface coating coats or modifies an inner surface of the separation region or a previously flowed material which coats the inner surface of the separation region.

27. The method of claim 1, the flowing step further comprising flowing one or more eluents or separation buffers into the separation region from one or more microchannels in fluid communication with the separation region.

28. The method of claim 27, further comprising varying a concentration of the one or more eluents or separation buffers flowed into the separation region to control separation of materials within the separation region.

29. The method of claim 1, further comprising sampling the enzyme, the enzyme substrate, and/or an additional material from one or more sources external to the microfluidic device.

30. The method of claim 29, wherein the additional material comprises one or more of: a modulator, an inhibitor, an antagonist, an agonist, an eluent, or a separation buffer.

31. The method of claim 30, wherein the one or more sources are present in a microtiter dish and wherein the microfluidic device comprises one or more external capillary elements in fluid communication with the separation region, the method comprising contacting the one or more external capillary elements to the one or more sources and drawing fluid out of the one or more sources, into the one or more external capillary elements, and into the microfluidic device.

* * * * *